United States Patent
Ben-Haim

(10) Patent No.: US 11,583,202 B2
(45) Date of Patent: Feb. 21, 2023

(54) FIELD GRADIENT-BASED REMOTE IMAGING

(71) Applicant: Navix International Limited, Road Town (VG)

(72) Inventor: Shlomo Ben-Haim, Milan (IT)

(73) Assignee: Navix International Limited, Road Town (VG)

( * ) Notice: Subject to any disclaimer, the term of this patent is extended or adjusted under 35 U.S.C. 154(b) by 332 days.

(21) Appl. No.: 16/638,773

(22) PCT Filed: Aug. 16, 2018

(86) PCT No.: PCT/IB2018/056158
§ 371 (c)(1),
(2) Date: Feb. 13, 2020

(87) PCT Pub. No.: WO2019/035023
PCT Pub. Date: Feb. 21, 2019

(65) Prior Publication Data
US 2021/0128009 A1    May 6, 2021

Related U.S. Application Data

(60) Provisional application No. 62/546,775, filed on Aug. 17, 2017.

(51) Int. Cl.
*A61B 5/00* (2006.01)
*A61B 5/0536* (2021.01)
*A61B 5/0538* (2021.01)

(52) U.S. Cl.
CPC .......... *A61B 5/0536* (2013.01); *A61B 5/0538* (2013.01)

(58) Field of Classification Search
CPC ..... A61B 5/0536; A61B 5/0538; A61B 5/063; A61B 5/283; A61B 5/4233; A61B 5/6852
See application file for complete search history.

(56) References Cited

U.S. PATENT DOCUMENTS

| | | | |
|---|---|---|---|
| 5,465,730 A | 11/1995 | Zadehkoochak et al. | |
| 5,553,611 A | 9/1996 | Budd et al. | |
| 5,662,108 A | 9/1997 | Budd et al. | |

(Continued)

FOREIGN PATENT DOCUMENTS

| | | |
|---|---|---|
| CN | 101219061 | 7/2008 |
| CN | 101868182 | 10/2010 |

(Continued)

OTHER PUBLICATIONS

Official Action dated Jun. 4, 2021 from the US Patent and Trademark Office Re. U.S. Appl. No. 16/338,710. (22 pages).

(Continued)

*Primary Examiner* — Mark D Remaly

(57) ABSTRACT

Systems and method for remote field measurement-based mapping of anatomical structures (e.g., using impedance image of electrical fields) are described. In some embodiments, an image of features within a target region is produced by analysis of a spatial pattern of field measurements made in a measurement region remote from the target region features; for example, but not exclusively, by treating the spatial arrangement of field measurements in some portion of the measurement region as indicating the spatial (e.g., angular and/or distance) arrangement of features (e.g., anatomical structure of topography and/or tissue type) in the target region.

32 Claims, 19 Drawing Sheets

(56) References Cited

U.S. PATENT DOCUMENTS

| | | | |
|---|---|---|---|
| 5,697,377 | A | 12/1997 | Wittkampf |
| 6,240,307 | B1 | 5/2001 | Beatty et al. |
| 6,640,119 | B1 | 10/2003 | Budd et al. |
| 6,728,562 | B1 | 4/2004 | Budd et al. |
| 6,826,420 | B1 | 11/2004 | Beatty et al. |
| 6,939,309 | B1 | 9/2005 | Beatty et al. |
| 6,947,785 | B1 | 9/2005 | Beatty et al. |
| 6,978,168 | B2 | 12/2005 | Beatty et al. |
| 6,990,370 | B1 | 1/2006 | Beatty et al. |
| 7,187,973 | B2 | 3/2007 | Hauck |
| 7,189,208 | B1 | 3/2007 | Beatty et al. |
| 7,996,060 | B2 | 8/2011 | Trofimov et al. |
| 2002/0077555 | A1 | 6/2002 | Schwartz |
| 2003/0018251 | A1 | 1/2003 | Solomon |
| 2005/0288586 | A1 | 12/2005 | Ferek-Petric |
| 2006/0084859 | A1 | 4/2006 | Johnson et al. |
| 2006/0247520 | A1 | 11/2006 | McGee |
| 2007/0049817 | A1 | 3/2007 | Preiss et al. |
| 2008/0190438 | A1 | 8/2008 | Harlev et al. |
| 2008/0242976 | A1 | 10/2008 | Robertson et al. |
| 2009/0005846 | A1 | 1/2009 | Zhu et al. |
| 2009/0171201 | A1 | 7/2009 | Olson |
| 2009/0171274 | A1 | 7/2009 | Harlev et al. |
| 2009/0262109 | A1 | 10/2009 | Markowitz et al. |
| 2009/0264778 | A1 | 10/2009 | Vitz et al. |
| 2012/0059249 | A1 | 3/2012 | Verard et al. |
| 2012/0078129 | A1 | 3/2012 | Bailin |
| 2012/0150046 | A1 | 6/2012 | Watson et al. |
| 2013/0079628 | A1 | 3/2013 | Groszmann et al. |
| 2014/0275913 | A1 | 9/2014 | Hill et al. |
| 2014/0275991 | A1 | 9/2014 | Potter et al. |
| 2016/0045133 | A1 | 2/2016 | Balachandran et al. |
| 2016/0113709 | A1 | 4/2016 | Maor |
| 2016/0242667 | A1 | 8/2016 | Fay et al. |
| 2018/0240237 | A1 | 8/2018 | Donhowe et al. |
| 2019/0336035 | A1 | 11/2019 | Dichterman et al. |
| 2020/0000368 | A1 | 1/2020 | Ben-Haim et al. |
| 2020/0085504 | A1 | 3/2020 | Schwartz et al. |
| 2020/0289025 | A1 | 9/2020 | Dichterman et al. |
| 2022/0329345 | A1 | 10/2022 | Kaplan |

FOREIGN PATENT DOCUMENTS

| | | |
|---|---|---|
| CN | 105491952 | 4/2016 |
| EP | 0974936 | 1/2000 |
| EP | 1767166 | 3/2007 |
| JP | 2003/527164 | 9/2003 |
| RU | 2009142646 | 3/2010 |
| WO | WO 98/01069 | 1/1998 |
| WO | WO 2006/055286 | 5/2006 |
| WO | WO 2008/097767 | 8/2008 |
| WO | WO 2010/129095 | 11/2010 |
| WO | WO 2011/142931 | 11/2011 |
| WO | WO 2012/092016 | 7/2012 |
| WO | WO2014/036439 | 3/2014 |
| WO | WO 2014/091418 | 6/2014 |
| WO | WO 2014/118535 | 8/2014 |
| WO | WO 2014/182822 | 11/2014 |
| WO | WO 2018/078540 | 5/2018 |
| WO | WO 2018/130974 | 7/2018 |
| WO | WO 2018/146613 | 8/2018 |
| WO | WO 2019/034944 | 2/2019 |
| WO | WO 2019/035023 | 2/2019 |

OTHER PUBLICATIONS

Notification Regarding Third-Party Preissuance Submission dated Jan. 29, 2021 From the US Patent and Trademark Office Re. U.S. Appl. No. 16/338,710.(2 Pages).

Third Party IDS Submission under 37 CFR 1.290 filed on Jan. 14, 2021 From the US Patent and Trademark Office Re. U.S. Appl. No. 16/338,710.(2 Pages).

Official Action dated May, 5, 2021 from the US Patent and Trademark Office Re. U.S. Appl. No. 16/476,875. (35 pages).

International Preliminary Report on Patentability dated May 9, 2019 From the International Bureau of WIPO Re. Application No. PCT/IB2017/056616. (8 Pages).

International Preliminary Report on Patentability dated Aug. 22, 2019 From the International Bureau of WIPO Re. Application No. PCT/IB2018/050784. (11 Pages).

International Preliminary Report on Patentability dated Jul. 25, 2019 From the International Bureau of WIPO Re. Application No. PCT/IB2018/050192. (8 Pages).

International Preliminary Report on Patentability dated Feb. 27, 2020 From the International Bureau of WIPO Re. Application No. PCT/IB2018/055344. (8 Pages).

International Preliminary Report on Patentability dated Feb. 27, 2020 From the International Bureau of WIPO Re. Application No. PCT/IB2018/056158. (8 Pages).

International Search Report and the Written Opinion dated Feb. 1, 2018 From the International Searching Authority Re. Application No. PCT/IB2017/056616. (14 Pages).

International Search Report and the Written Opinion dated Jan. 2, 2019 From the International Searching Authority Re. Application No. PCT/IB2018/056158. (16 Pages).

International Search Report and the Written Opinion dated May 9, 2018 From the International Searching Authority Re. Application No. PCT/IB2018/050192. (16 Pages).

International Search Report and the Written Opinion dated Sep. 25, 2018 From the International Searching Authority Re. Application No. PCT/IB2018/050784. (18 Pages).

International Search Report and the Written Opinion dated Nov. 30, 2018 From the International Searching Authority Re. Application No. PCT/IB2018/055344. (15 Pages).

Invitation to Pay Additional Fees, Communication Relating to the Results of the Partial International Search and the Provisional Opinion dated Jun. 26, 2018 From the International Searching Authority Re. Application No. PCT/IB2018/050784. (13 Pages).

Boston Scientific "Rhythmia™ Mapping System: Rhythmia Disposables Product Information: Intellamap Orion™ High Resolution Mapping Catheter", Boston Scientific, 2 P., Sep. 2015.

Crospon "Esophageal Treatment by Esoflip®", Crospon, Product Sheet, 4 P., 2017.

Crospon "Flip® Technology", Crospon, Product Sheet, 6 P., 2017.

Hilbert et al. "An Integrative Approach to Slow Pathway Modulation in AVNRT Using A Novel Ultra High-Density Electroanatomical Mapping System", Clinical Research in Cardiology. XP035518036, 104(8): 697-699, Published Online Mar. 31, 2015.

Myronenko et al. "Non-Rigid Point Set Registration: Coherent Point Drift", Advances in Neural Information Processing Systems, NIPS, 19: 1009-1016, 2009.

The State Intellectual Property Office of the People's Republic of China Re. Application No. 201880064206.7. (7 Pages).

Official Action dated Oct. 6, 2022 from the US Patent and Trademark Office Re. U.S. Appl. No. 16/639,610. (44 pages).

Notification of Office Action and Search Report dated Nov. 10, 2022 From the State Intellectual Property Office of the People's Republic of China Re. Application No. 201880055476.1 and its Summary in English. (15 Pages).

Bailin et al. "Direct Visualization of the Slow Pathway Using Voltage Gradient Mapping: A Novel Approach for Successfid Ablation of Atrioventricular Nodal Reentry Tachycardia", EP Europace, 13(8): 1188-1194, Pubhshed Apr. 19, 2011.

Casella et al. "Rationale and Design of the NO-PARTY Trial: NearZero Fluoroscopic Exposure During Catheter Ablation of Supraventricular Arrhythmias in Young Patients". Cardiology in the Young. 22(5): 539-546. Sep. 13, 2012.

Eitel et al. "EnSite Elocity™ Cardiac Mapping System: A New Platform for 3D Mapping of Cardiac Arrhithmias", Expert Review of Medical Devices, 7(2): 185-192, Published Jan. 9, 2014.

Guo et al. "Current Researches and Capabilities of Multifunctional Intracardiac Echocardiography", Journal of China Clinical Medical Imaging,. 20( 11): 848-850, Published Nov. 20, 2009. (Chinese only).

(56) References Cited

OTHER PUBLICATIONS

Zhang "Virtual Heart: Modeling of Anatomy and Electrophysiology", Chinese Master's Theses Full-text Database(CMFD): 268P., Apr. 15, 2009. (Chinese only).

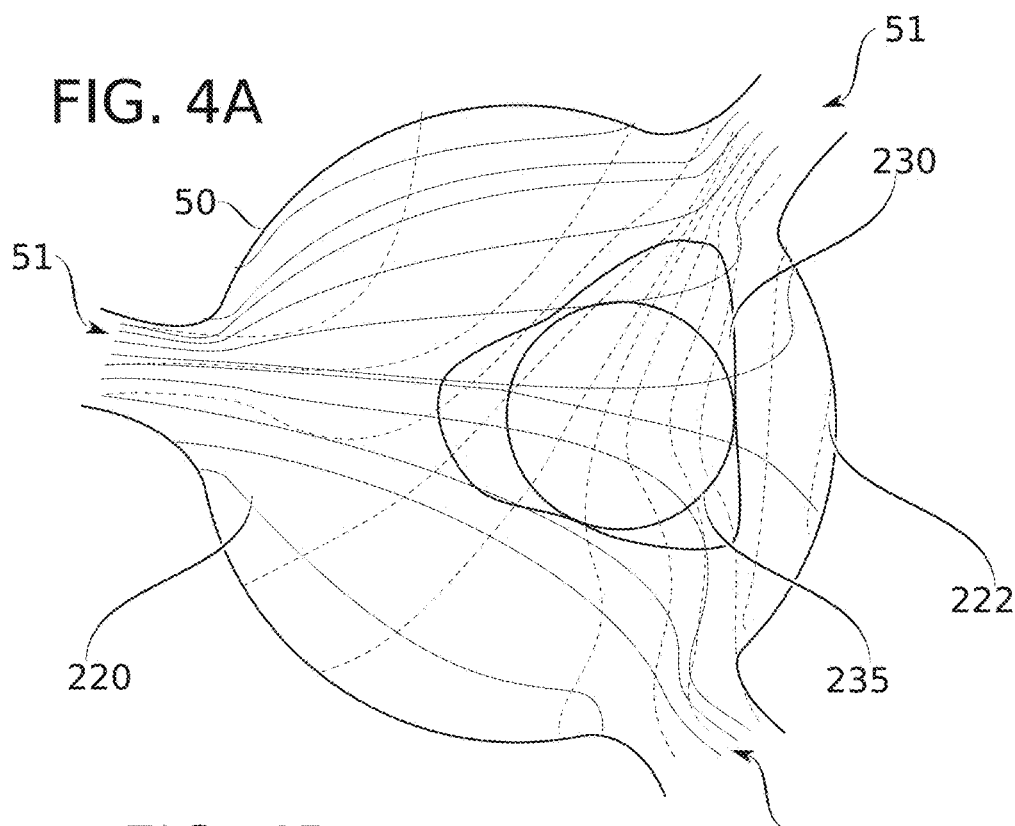
FIG. 4A
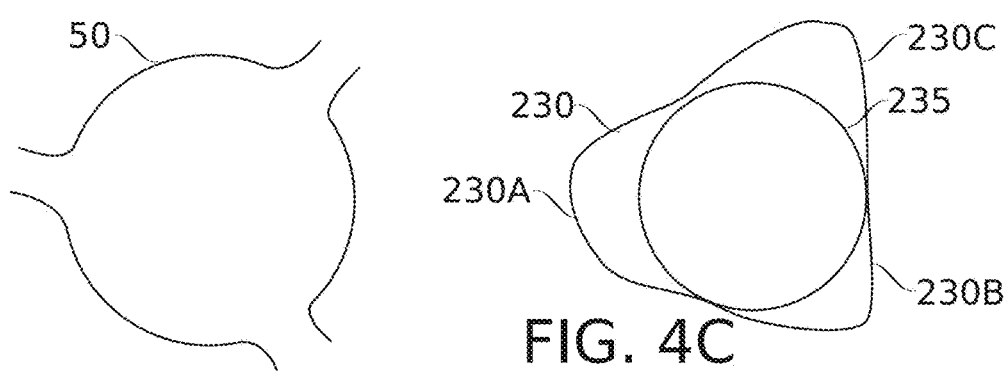
FIG. 4B
FIG. 4C
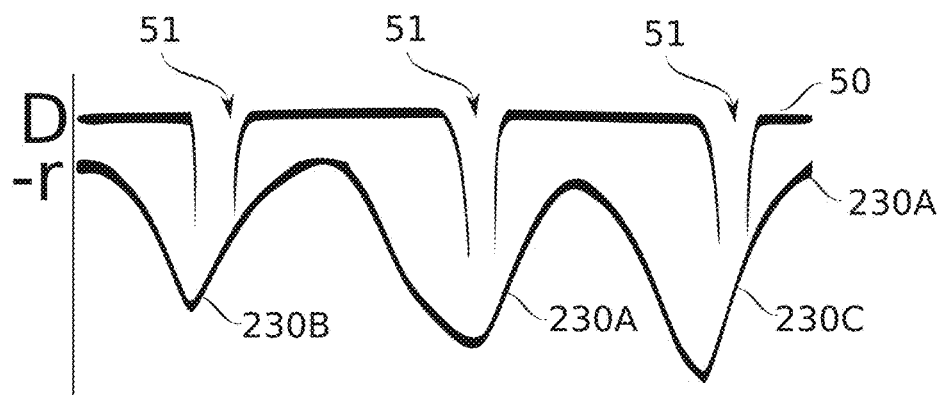
FIG. 4D

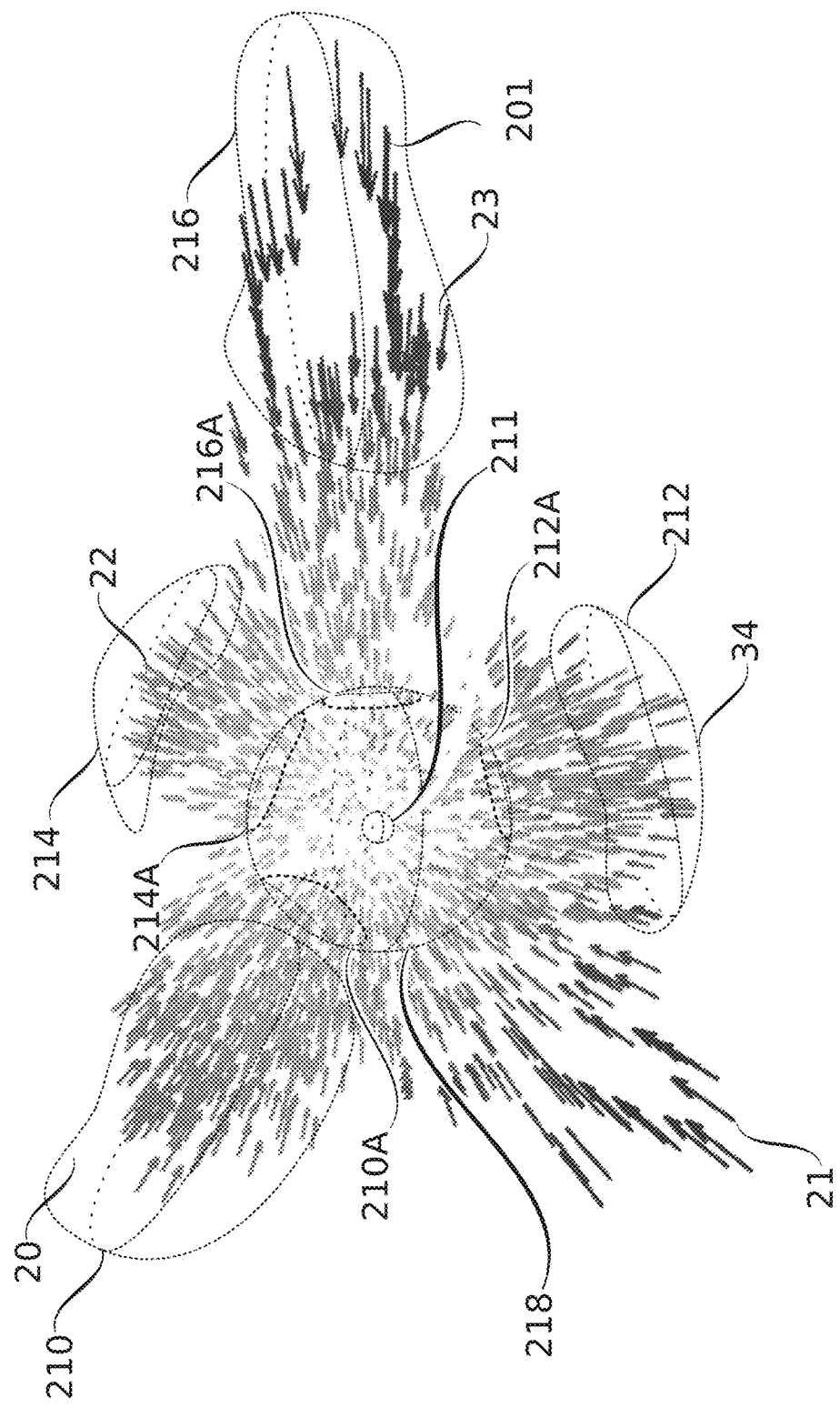

FIELD GRADIENT-BASED REMOTE IMAGING

RELATED APPLICATIONS

This application claims benefit of priority under 35 USC § 119(e) of U.S. Provisional Patent Application No. 62/546,775 filed Aug. 17, 2018, the contents of which are included herein by reference in their entirety.

FIELD AND BACKGROUND OF THE INVENTION

The present invention, in some embodiments thereof, relates to the field of anatomical mapping, and more particularly, to non-contact anatomical mapping of internal body structures.

In many interventional medical procedures, the operator can benefit by having the ability to image in real-time the anatomy in the relevant vicinity of the action field of the procedure. In cardiac electrophysiology mapping in particular (e.g., for cardiac electrophysiology ablation as well as in other interventional cardiac procedures), multiple technologies exist for providing real-time imaging of the action field.

Intra-procedure imaging technologies include those that can image remotely from a chamber wall, and those that can reconstruct a chamber wall using the knowledge of the location of multiple points on the wall or multiple points within the chamber, or a combination of the last two.

An intra-cardiac ultrasound probe, for example can generate an image of the wall of a chamber from a remote location within the chamber.

Navigable catheters (e.g., electrode catheters) may be used to acquire measurements from multiple locations of the chamber wall. Related prior art includes International Patent Publication No. WO2010129095A2, which relates to "the determination and representation of anatomical information and/or physiological information relating to a heart using, e.g., a non-contact catheter."

SUMMARY OF THE INVENTION

There is provided, in accordance with some embodiments of the present invention. a method of producing an image using measurements of at least one electrical field made within a first region of a body, the method comprising: for each of the at least one electrical fields: receiving a plurality of measurements of voltages of the electrical field measured using an intrabody probe at different positions within the first region, and mapping voltage gradients of the electrical field, using the voltage measurements; and producing an image showing features located in a second region of the body and outside of the first region, based on the mapping.

In some embodiments, the received measurements were obtained using a plurality of electrodes positioned at known distances along the intrabody probe, and the voltage gradients indicated by the voltage measurements are determined based on the voltage measurements and the known distances.

In some embodiments, the voltage gradients comprise a plurality of different local voltage gradients within the first region.

In some embodiments, the producing an image uses voltage gradients from near a periphery of the first region, the near periphery being defined to exclude voltage gradients from a central portion of the first region.

In some embodiments, nearness to the periphery is defined by parameters of a rolling ball algorithm.

In some embodiments, the producing the image indicates distances from the first region to features as a function of gradient strength near the periphery.

In some embodiments, the producing the image indicates feature distances from the first region based on a map of voltage gradient strength near the periphery as a function of solid angle.

In some embodiments, the producing the image indicates distances from the first region to features of the image as a function of a decay of a distortion in voltage gradients with distance.

In some embodiments, the method comprises producing a plurality of images corresponding to a corresponding plurality of different heartbeat phases, based on a heartbeat phase during which the voltage measurements were measured.

In some embodiments, the method comprises: making contact measurements of a surface of the second region; and identifying a feature of the image which indicates an anatomical structure located behind the surface of the second region, based on a mismatch between the position of the surface as measured by contact measurement and a position of same surface as indicated in the image.

In some embodiments, the image is produced within about 5 seconds of receiving the first measurements.

In some embodiments, a plurality of respectively corresponding portions of the first region and of the imaged second region are in correspondence based on their shared angular position with respect to a reference location.

In some embodiments, the plurality of respectively corresponding portions of the first region are between the reference location and respective portions of the second region corresponding to the respectively corresponding portions of the first region.

In some embodiments, a plurality of respective portions of the first region and of the image are in correspondence, such that the image portions are each respectively indicated by measurements from the respective corresponding portion of the first region.

In some embodiments, the producing comprises processing of the measurements to isolate differences among gradients at positions within the first region.

In some embodiments, the second region comprises a lumenal wall of a body cavity.

In some embodiments, the lumenal wall is a wall of a cardiovascular lumen.

In some embodiments, the cardiovascular lumen comprises a left atrium.

In some embodiments, the first region comprises a region within the body cavity and at a distance from the lumenal wall of at least 1 cm.

In some embodiments, the image is presented as a 3-D surface of the second region.

In some embodiments, the features shown by the image comprise structure of tissue within the second region.

In some embodiments, the features shown by the image comprise features of the topography of a lumenal wall within the second region.

In some embodiments, the features of the topography of the lumenal wall comprise an aperture in the lumenal wall.

In some embodiments, the features of topography of the lumenal wall comprise a ridge along at least a portion of the lumen wall.

In some embodiments, the features located in the second region of the body are at a distance from the first region of at least 1 cm.

In some embodiments, the mapping produces a map of the voltage gradients of the electrical field, and the image is generated using the map.

In some embodiments, the at least one electrical field comprises at least three electrical fields crossing within the first region.

There is provided, in accordance with some embodiments of the present invention. a method of producing an image using measurements of at least one electrical field made within a first region of a body, the method comprising: for each of the at least one electrical fields: receiving a plurality of measurements of voltages of the electrical field measured using an intrabody probe at different positions within the first region, each of the different positions being away from an aperture inside the body, and on a same side of the aperture, and mapping voltage gradients of the electrical field, using the voltage measurements; and producing an image showing the aperture of the body, based on the mapping.

In some embodiments, the received measurements were obtained using a plurality of electrodes positioned at known distances along the intrabody probe, and the electrical field gradients indicated by the voltage measurements are determined based on the electrical field data and the known distances.

In some embodiments, the voltage gradients comprise a plurality of different local voltage gradients at the different positions.

In some embodiments, the producing includes indicating a distance of the aperture in the image from the first region as a function of a decay of a distortion in voltage gradients with distance.

In some embodiments, the method comprises producing a plurality of images corresponding to a corresponding plurality of different heartbeat phases, based on a heartbeat phases during which the voltage measurements were measured.

In some embodiments, the image is produced within about 5 seconds of receiving the first measurements.

In some embodiments, a plurality of portions of the aperture shown in the produced image correspond to the different positions based on their shared angular position with respect to a reference location.

In some embodiments, the different positions are positioned between the reference location and respective portions of the aperture.

In some embodiments, the different positions and portions of the image are in respective correspondence, such that the image portions are each respectively indicated by measurements from the respective corresponding positions.

In some embodiments, the producing comprises processing of the measurements to isolate differences among gradients at the different positions.

In some embodiments, the aperture is within a lumenal wall of a body cavity.

In some embodiments, the lumenal wall is a wall of a cardiovascular lumen.

In some embodiments, the cardiovascular lumen comprises a left atrium.

In some embodiments, a region comprising the different positions comprises a region within the body cavity and at a distance from the lumenal wall of at least 1 cm.

In some embodiments, the image includes a presentation of a 3-D surface defining the aperture.

In some embodiments, the features shown by the image comprise structure of tissue defining the aperture.

In some embodiments, features shown by the image comprise features of the topography of a lumenal wall defining the aperture.

In some embodiments, the features of topography of the lumenal wall comprise a ridge along at least a portion of the lumen wall.

In some embodiments, the at least one electrical field comprises at least three electrical fields crossing within the first region.

There is provided, in accordance with some embodiments of the present invention. an imaging system configured to produce an image using measurements of at least one electrical field made within a first region of a body, the imaging system comprising a processor and memory configured with processing instructions to: for each of the at least one electrical fields: receive a plurality of measurements of voltages of the electrical field measured using an intrabody probe at different positions within the first region, and produce a map of voltage gradients of the electrical field, using the voltage measurements; and produce an image showing features located in a second region of the body and outside of the first region, based on the map.

In some embodiments, the imaging system comprises an electrical field measurer configured to measure the voltage measurements.

In some embodiments, the imaging system comprises a position tracker configured to measure the positions of the intrabody probe at the different positions.

In some embodiments, the imaging system comprises a display configured to display the produced image.

There is provided, in accordance with some embodiments of the present invention. a method of producing an image, using an intrabody probe measuring fields at different positions in a first region of a body, the method comprising: measuring data indicative of at least one electrical field using an electrode of the intrabody probe when the electrode is at different positions within the first region; associating the measured data with data indicative of the different positions, so that each measured electrical field indication is associated with a respective position indication; and producing an image showing features located in a second region of the body distanced from the first region by at least 1.5 cm, based on the associated positions and electrical field data.

In some embodiments, the measuring comprises determining electrical field gradients at the different positions within the first region, and the producing is based on the determined electrical field gradients.

In some embodiments, the measuring is performed using a plurality of electrodes positioned at known distances along the intrabody probe, and the determining of electrical field gradients is based on the electrical field data and the known distances.

In some embodiments, a plurality of respectively corresponding portions of the first region and of the imaged second region are in correspondence based on their shared angular position with respect to a reference location.

In some embodiments, the portions of the first region are between the reference location and respective portions of the second region corresponding to the respectively corresponding portions of the image.

In some embodiments, a plurality of respective portions of the first region and of the image are in correspondence, such that the image portions are each respectively indicated by measurements from the respective corresponding portion of the first region.

In some embodiments, the producing comprises processing of the measurements to isolate differences among gradients at the different portions of the first region.

In some embodiments, the second region comprises a lumenal wall of a body cavity.

In some embodiments, the lumenal wall is a wall of a cardiovascular lumen.

In some embodiments, the cardiovascular lumen comprises a left atrium.

In some embodiments, the first region comprises a region within the body cavity and away from contact of the intrabody probe with the lumenal wall.

In some embodiments, the probe is a basket electrode probe.

In some embodiments, the image is presented as a 3-D surface of the second region.

In some embodiments, the image is presented as an interior view of the 3-D surface.

In some embodiments, the method comprises presenting an indication of a position of the intrabody probe, relative to structures of the second region.

In some embodiments, the surface of the second region comprises a lumenal surface of the second region, and the image is presented as a 3-D relief map of the surface of the second region flattened to allow viewing of at least 80% of a total angular extent of the lumenal surface.

In some embodiments, the features indicated by the image comprise structure of tissue within the second region.

In some embodiments, the features indicated by the image comprise features of the topography of a lumenal wall within the second region.

In some embodiments, the features of the topography of the lumenal wall comprise an aperture in the lumenal wall.

In some embodiments, the features of topography of the lumenal wall comprise a ridge along at least a portion of the lumen wall.

In some embodiments, the features of topography of the lumenal wall comprise an indentation along the lumen wall.

In some embodiments, the indicated structure of tissue comprises indications of the tissue type composition of a lumenal wall within the second region.

In some embodiments, the features indicated by the image comprise electrical transmission properties of tissue in a lumenal wall within the second region.

In some embodiments, the features located in a second region of the body are at a distance from the first region of at least 2 cm.

There is provided, in accordance with some embodiments of the present invention. a method of producing an image using an intrabody probe positioned in a body region, the method comprising: measuring, using electrodes of the intrabody probe and from within a first region of a body, data indicative of electrical fields induced within the body; producing a first image showing features of a second region outside of the first region, based on the measuring; continuing the measuring within the first region of the body; and producing a second image showing features of the second region outside of the first region, based on the measuring and the continued measuring.

In some embodiments, the method comprises positioning of the intrabody probe within the first region and manipulating the intrabody probe to move across the first region.

In some embodiments, the moving across the first region comprises relative movements with respect to the body due to heart contractions and breathing motions, during the measuring.

In some embodiments, the moving across the first region comprises a plurality of reorientations of the intrabody probe while travelling generally across the first region.

In some embodiments, the method comprises getting closer to the second region before and/or during, the continuing the measuring.

In some embodiments, at least some measurements used in the producing the second image are from positions within the first region closer to some corresponding positions of the second region indicated in the image than any measurement positions within the first region used in producing the first image and also corresponding to the same portions of the second region indicated in the image.

In some embodiments, the producing the second image comprises using the measurements from positions within the first region closer to the corresponding positions of the second region indicated in the image, thereby producing a second image which indicates a view of the second region in greater detail than the first image.

In some embodiments, the method comprises presenting at least one of the images along with an indication of relative image quality among different positions of the image.

In some embodiments, the indication comprises an indication of sampling density.

In some embodiments, the indication comprises an indication of variability.

In some embodiments, the indication of variability is an indication of measurement change as a function of measurement position proximity to the second region, for measurement positions of the first region sharing corresponding positions within the at least one of the images.

In some embodiments, the method comprises presenting the second image along with an indication of relative image quality at different positions of the image compared to the first image.

In some embodiments, the method comprises presenting at least the second image with an indication of a number of measurement samples used in the producing.

In some embodiments, the method comprises presenting the second image with an indication of measurement samples used in the producing taken from positions in the first region closer to corresponding positions in the second region that used in producing the first image.

In some embodiments, the third image is based on the measurements of at least the first image as well as further measurements made with the probe in contact with a surface of the second region.

There is provided, in accordance with some embodiments of the present invention. a method of estimating a position of an intrabody probe, comprising: measuring, using electrodes of the intrabody probe and from within a first region of the body, data indicative of electrical fields induced within the body; and producing a map indicating features of a second region remote from the first region, based on the measuring; receiving an image of the second region; registering the map to the image; and showing a position of the probe on the registered image, based on the registering.

In some embodiments, the received image is previously produced for the second region by performing the measuring and the producing from a reference region remote from the second region.

In some embodiments, the reference region substantially overlaps the first region.

In some embodiments, the reference region extends radially beyond the first region towards the second region.

In some embodiments, the received image comprises a CT or MRI image of the second region.

In some embodiments, the received image comprises a 3-D reconstruction of the second region.

In some embodiments, the position estimate comprises an angular position estimate, relative to a position located away from the second region.

In some embodiments, the position estimate comprises estimation of distance from the second region.

There is provided, in accordance with some embodiments of the present invention. a method of guiding an intrabody probe to a target, comprising: measuring, using electrodes of the intrabody probe and from within a first region of the body, data indicative of electrical fields induced within the body; and producing a first estimate indicating at least one estimated feature of a second region remote from the first region, based on the measuring; selecting a target direction to reach a target portion of the second region, based on the first estimate; moving the intrabody probe in the target direction to a subsequent region of the body; continuing the measuring within the subsequent region; producing a subsequent estimate indicating estimated features of the second region based on the continued measuring; re-selecting a target direction to reach the target portion, based on the subsequent estimate; and repeating the moving, continued measuring, producing based on the continued measuring, and re-selecting, to reach the target portion with the intrabody probe.

In some embodiments, the first estimate and any subsequent estimate comprise images.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present disclosure may take the form of a computer program product embodied in one or more computer readable medium(s) having computer readable program code embodied thereon. Implementation of the method and/or system of some embodiments of the disclosure can involve performing and/or completing selected tasks manually, automatically, or a combination thereof. Moreover, according to actual instrumentation and equipment of some embodiments of methods, systems, and/or computer program products of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In an exemplary embodiment, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWINGS

Some embodiments of the present disclosure are described, by way of example only, with reference to the accompanying drawings. With specific reference now to the drawings in detail, it is stressed that the particulars shown are by way of example, and for purposes of illustrative discussion. In this regard, the description taken with the drawings makes apparent to those skilled in the art how embodiments of the present disclosure may be practiced.

In the drawings:

FIGS. 4A-4D schematically illustrate the conversion of measurement results (obtained, for example, as shown in FIGS. 3A-3D) into a representation (e.g., a map, reconstruction and/or image) of a body region, according to some embodiments of the present disclosure;

FIG. 5A schematically illustrates an example of the spatial distribution of local electrical field gradient magnitudes and directions in a heart chamber, according to some embodiments of the present disclosure;

DESCRIPTION OF SPECIFIC EMBODIMENTS OF THE INVENTION

Figure 1:
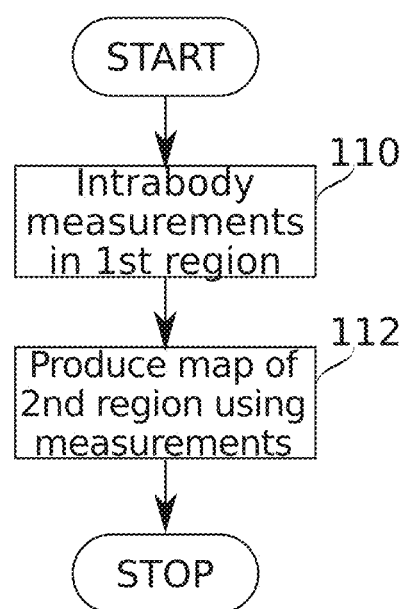
FIG. 1 is a flowchart schematically illustrating a method for remote field-sensing mapping of a region of a body region using an intrabody probe, according to some embodiments of the present disclosure.

The present invention, in some embodiments thereof, relates to the field of anatomical mapping, and more particularly, to non-contact anatomical mapping of internal body structures.

Overview

A broad aspect of some embodiments of the present disclosure relates to the visualization of body regions using field gradients sensed by a probe at indicated probe positions. Optionally, the probe is inside the body during a medical procedure, e.g., a procedure performing medical treatment using the probe, and/or a procedure guided based on information received from the probe.

The inventors have found that combined position and field gradient information may be used to yield surprisingly detailed information about anatomical features even several centimeters away from positions that have actually been traveled through (also referred to herein as visited) by a sensing probe. In some embodiments, the information is transformed into images, optionally images that begin as rough indications of a probe's anatomical environment, then evolve over time to reveal new structure as new information is received, e.g., as new measurements are taken. Moreover, the new measurements may be directed, in some embodiments, to particular targets within the environment: from a distance (e.g. by "pointing" the probe at the target), from nearby (e.g., less than 1 cm from a target) measuring and/or during contact of the probe with a surface of the target. The result, in some embodiments, is an image that becomes more detailed in specific response to target-seeking and/or -indicating probe-movements, many of which are anyway performed naturally in the course of the procedures.

An aspect of some embodiments of the present invention relates to mapping of a target body region (also referred to herein a second body region) using measurements of a field from positions remote from the target body region and within a measurement body region (also referred to herein as a first body region). In some embodiments, the measurements comprise data indicative of interactions of an electrical field with field-affecting (e.g., field-distorting) features in the target body region. Measurements indicative of an electrical field are optionally measurements of voltage, phase, impedance, flux, and/or another electrical field parameter.

In some embodiments, an image is produced from a map of the target region, wherein the map comprises, for example, a mapping of measurements to associated positions. In general, reference herein to something as an image emphasizes its role as being displayed/displayable; and reference herein to something as a map emphasizes its role as encoding at least one spatially distributed property. For example, herein, the term "map" refers to images and/or data structures which illustrate/encode relationships between locations in space and values of one or more properties associated with those locations. The properties associated with the locations may be determined by measurements. An "image", in some embodiments, comprises a data structure or physical object which is displayable and/or displayed for viewing as a depiction of an image subject. The data structure may include, in some embodiments, raster data and/or vector drawing commands. An image may also be a map. Herein, instances of maps used, in some embodiments, comprise mappings of measured electrical field properties to positions. Instances of images, in some embodiments of the present disclosure, include images generated using one or more maps of the image subject. In some embodiments, the object may be a spatially extended body cavity. In some embodiments, an image of an object may be generated using a map by assigning brightness and/or color values to spatial locations in the image, depending on property values associated with these spatial locations in the map. As explained herein, it is a particular characteristic of some embodiments of the present invention that an image of a region, such as an image of a body cavity shape or another arrangement of body tissues, is generated using a map of some other region. For example, the mapped region may be an interior portion of a body cavity out of contact with the body cavity's surface, and the image produced from that map may be of a surface of that body cavity. In another example, the mapped region may be an interior portion of a body cavity having a surface with an aperture leading to outside of the body cavity, and the image produced from the map may include the aperture and at least some of the region outside the body cavity, to which the aperture leads. The measurement-associated positions may be defined relative to a reference position within the measurement region. For example, the positions may be defined by specifying for each position a solid angle pointed from the reference point towards the target region. In some embodiments, a map is produced from the measurements via another method, for example an iterative reconstruction technique.

In some embodiments, distances between one or more mapped portions of the target body region and any region in the measurement body region are at least, for example, 1 cm, 1.5 cm, 2 cm, 2.5 cm, and/or 3 cm. In some embodiments, the distance is at least 10×, 15×, 20×, 25×, and/or 30× the maximum size of a sensor used, such as an electrode.

In some embodiments, the mapped portions of the target body region are in correspondence with portions of the measurement body region, in the sense that measurements in the measurement body region can be processed into direct indications of conditions in corresponding portions of the target body region. For example, the measurements may indicate characteristics of corresponding portions of the target body region. In another example, measurements indicate features of the target region portions (such as material and/or topographical structure) which are themselves highly correlated with the measurements.

In some embodiments, features to be mapped (e.g., vein entrance, valve, ridge, etc.) influence the fields both locally and remotely. The remote influence may include influencing the field in the first body region, within which the fields are measured in order to obtain a map of the features. At a location similarly remote from a number of different features, the fields are influenced by a number of the features. In some embodiments, differences in field measurements taken at other positions in the first body region are attributable to a feature at a particular angular direction and/or distance from the first body region. In some embodiments, characteristics of the mapped portions are determined by solving the "inverse problem", for example as described in relation to FIG. 1, to distinguish and localize the remote positions of the features to be mapped that influence the fields within the first body region. The inverse problem may be solved, for example, by a reconstruction method; optionally, an iterative reconstruction method.

In some embodiments, differences among measurements at different positions indicate a difference in a local field gradient obtained from the measurements. That is: the measurements define local field gradients for a plurality of different locations, and there are differences, at different positions, between these local field gradients.

Optionally, the local field gradient is expressed as a partial derivative of a scalar field characteristic; for example voltage gradient over space as $\partial V/\partial R$ (actual gradient measurements will be of finite differences, but partial derivative notion is used for purposes of explanation). Optionally or additionally, another gradient is used, for example a spatial gradient of voltage over field frequency $\partial(\partial V/\partial f)/\partial R$, and/or field phase $\partial(\partial V/\partial \Phi)/\partial R$. Optionally, the spatial gradient is of a complex field characteristic such as impedance. In some embodiments, the field gradient used is of any suitable field measurement of a radio frequency electromagnetic field signal. In some embodiments, the measurements within the first body region are obtained within a portion of a body cavity, such as a heart chamber (e.g., a cavity within a left atrium), which is itself surrounded by anatomical structures of the second region (e.g., tissues of a left atrial lumenal wall, apertures thereof, neighboring portion of an esophagus, etc.).

Throughout the description and claims, reference to first and second regions, or similarly to measurement region and target region are references to two different regions. While the two different regions might partially overlap, they never mutually overlap completely. In some embodiments, at least one feature or landmark in the target region is not within the measurement region, so that at least one mapped feature is not visited by the probe. In some embodiments, each location of one region is at least 1 cm from every location of the other region, for example, 1 cm, 1.5, 2, 2.5, 3, or more centimeters from every location of the other region.

Measurements that measure local gradients (e.g., local voltage gradients), in some embodiments, may be obtained between two measurement positions separated by no more than about 1 mm, 2 mm, 3 mm, 4 mm, 5 mm, or 10 mm.

In some embodiments, an image of the target body region is produced to represent an estimation of one or more aspects of anatomical structure of the target body region. In some embodiments, the anatomical structure represented comprises topography of the anatomical structure; for example a surface marking a boundary between two tissue types, tissue and fluid, tissue and air, or another surface. In some embodiments, the topography imaged comprises the topography of an interior surface of a body cavity, optionally including indications of apertures of the body cavity and/or lumens connected to the body cavity. Optionally, the topography is indicated at a low spatial resolution, for example, indicating the general angular and/or distance positions of features such as apertures and/or indentations. In some embodiments, the general angular position is provided by solid angles at solid angle resolution corresponding to a cone having a base angle of more than 20°, 25°, 30°, 35°, or 45°. Optionally, the fidelity of the topography represented to actual anatomy is increased by the use of reconstruction constraints; for example a volume, width, height, length, and/or other measurement obtained from an echocardiogram, MRI, and/or CT scan.

In some embodiments, influences from field-affecting features (and in particular, anatomical structures acting as field-affecting features) comprise influences on field phase, gradient, and/or amplitude; moreover the influences may vary as a function of parameters of the field itself such as frequency.

In some embodiments, anatomical structure representation includes representation tissue types, and thus may be indicative of, for example, cellular structure differences between healthy and unhealthy tissue, and/or differences in one or more functional properties. Optionally, an anatomical structure represented in the image comprises an inner surface of a heart chamber (for example, a left atrium), and the tissue type difference comprises a difference between viable myocardial tissue, and fibrotic tissue. Optionally, the functional properties comprise electrical transmission properties of myocardial tissue.

In some embodiments, the map is produced as an estimate of the angular position of features in the mapped region remote from the measurement region, without particular reference to absolute distance. For example, the field measurement data is treated in the map as describing features on a sphere of arbitrary size. Optionally, this includes a relationship of correspondence, such that portions of the measurement region have corresponding parts in the mapped region, via a shared angular position within the map. Optionally, this arbitrary-size sphere is used as a preliminary reconstruction of the 3-D shape of the mapped region.

Optionally, the arbitrary-size sphere reconstruction is further shaped using the field data, for example, using an assumption that larger field concentrations and/or field gradients correspond to angles where features of the mapped region are more distant. In some embodiments, an image of the reconstruction reconfigures the appearance of the reconstruction geometry to provide a panoramic (partially flattened) view of the mapped region, e.g., to allow simultaneous viewing of substantially the entire surface defining a 3-D body region.

An aspect of some embodiments of the present invention relates to mapping of a target body region using measurements from field-sensing probe which moves to sample a measurement region, in order to obtain data for mapping a target region, remote from the measurement region, and then produce a map revealing structural information about the remote target region. The map of the target region is produced by analysis of the spatial pattern of field measurements made in the measurement region; for example, but not exclusively, by treating the spatial arrangement of field measurements in some portion of the measurement region as indicating the spatial (e.g., angular and/or distance) arrangement of features (e.g., anatomical structure of topography and/or tissue type) in the target region.

In some embodiments, the measurement region is smaller than the second target region, with such a relative size difference that the measurement region is everywhere substantially remote (e.g., at least 1 cm, 1.5 cm, 2 cm, 2.5 cm, 3 cm, or another distance) away from at least portions of the mapped target region. In some embodiments, the measurement region is no more than 10% of the volume subtended by the target region (e.g., the volume substantially enclosed by a lumenal wall of the target region), or optionally no more than 10%, 20%, 40%, or 50%, of the target region. In some embodiments, the measurement region occupies a central region of a lumen defined by a lumenal wall of the target region, wherein the map produced is a map of features of the lumenal wall and/or apertures thereof. In some embodiments, the measurement region is positioned to one side of an aperture which is imaged; for example, the measurement region is all of: inside the body, away from an aperture inside the body (that is, not touching a plane defined by a periphery of the aperture), and on a same side of the imaged aperture (e.g., not crossing that plane). Apertures to a body cavity in particular may include, in some embodiments, places at which blood vessels attach to the body cavity, valves of the body cavity, openings to an outer surface of the body, or another opening in a wall of the body cavity such as a puncture, incision, and/or foramen.

An aspect of some embodiments of the present invention relates to guidance of a probe to lumenal wall targets (in a target region) based on indications of the directions from the probe to lumenal wall landmarks. The indications may be updated as a function of proximity of the probe to the indicated landmarks.

Again, and also for the other aspects to follow, the map of the target region is produced, in some embodiments, by analysis of the spatial pattern of field measurements made in a measurement region remote from the target features; for example, but not exclusively, by treating the spatial arrangement of field measurements in some portion of the measurement region as indicating the spatial (e.g., angular and/or distance) arrangement of features (e.g., anatomical structure of topography and/or tissue type) in the target region.

In some embodiments, remote field maps do not necessarily give precise angular appearances of lumenal wall targets which are broadly revealed in the map by their remote influences on local field conditions. However, after motion of a measurement probe, e.g., in the estimated direction of such a target, or in any other direction, it is possible to obtain new measurements which potentially establish a new angular appearance for the field-influencing feature of interest. This appearance may be shown in a new image generated based on a map updated to include information from the new measurements. Additionally or alternatively, the map is used in a non-imaging mode, for example, used to generate a direction indication (such as an arrow or other marker), and/or navigation instructions (for use by a human user and/or automatically by a robotic manipulator).

An aspect of some embodiments of the present invention relates to position finding using the positions of landmark features relative to each other in a map of electrical field distortions mapped to locations in a measurement region while being influenced by features of a target region outside of the measurement region. Herein, the phrase "distortions influenced by X"—with respect to distortions of an electrical field, and wherein "X" is a phrase referring to a structure such as tissue and/or features thereof such as an aperture—refers specifically to effects on the distribution of a property such as voltage in the electrical field which are due to (i.e., would disappear without) the interaction of the electrical field with the referent of "X". Similarly, if the referent of "X" were different (e.g., in shape and/or composition), the distortions would be different. Furthermore, the distortions may include in particular distortions in portions of the electrical field which are at positions different than (e.g., remote from by at least 1 cm, 2 cm, or 3 cm) the referent of "X".

In some embodiments, the position finding comprises registering data other than relative positions of the landmarks. For example, data from a CT and/or MRI image showing certain landmarks is registered to the current position of the probe, based on locations of corresponding landmarks measured using the probe, such as topographical landmarks in the remote field map.

An aspect of some embodiments of the present invention relates to the use of remote field mapping to establish an initial rough map, optionally using general motion in a measurement region remote from the target region, followed by additional motions of the probe for measuring in more detail certain target regions. In some embodiments, the result is used to produce an image which is selectively enhanced in the more closely-visited regions.

Optionally, the enhanced image is also modified to include measurements indicating positions where contact is made by the probe with the map target region.

An aspect of some embodiments of the present invention relates to the estimation of lumenal wall structure. The estimation may include attributing measured properties of electrical field properties sensed from within a region of the lumen to a representation of the lumenal wall.

As used herein, the term "reconstruction" is used to indicate a process of generating a representation of a three dimensional shape of a target (a body cavity shape, in some embodiments of the present invention), based on indications of positions within and/or surfaces of the target, optionally supplemented by further information such as a template shape that is transformed to match available position data, and/or other measurements of a template shape. In some embodiment, the representation comprises and/or is presentable as an image of the target shape.

Herein the term "constraint" is used in several descriptions to refer to information and/or assumptions that limit possible positions of, configurations of and or/relationships among measurements obtained at potentially unknown positions in space. Constraints are optionally not used as "hard constraints", e.g., simultaneous measurements from a plurality of electrodes said to be "constrained" at fixed distances from each other may be placed at slightly different distances in an actual reconstruction, due, for example, to measurement errors, competing constraints, features of an algorithm used for minimization of error in assigned positions, etc.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Remote Imaging Based on Position-Referenced Sets of Field Measurements General Method Measuring Reference is now made to FIG. 1, which is a flowchart schematically illustrating a method for remote field-sensing mapping of a region of a body region using an intrabody probe, according to some embodiments of the present disclosure. In some embodiments, the field-sensing mapping comprises impedance mapping by an intrabody electrode probe. The mapping is optionally of any structural aspect of the anatomy which is suitably revealed by influences on measurements of the sensed field.

At block 110, the flowchart begins. An intrabody probe is used to obtain intrabody measurements of an induced field; optionally, a plurality of induced fields. These measurements are referred to herein as a measurement set. In some embodiments, induced field(s) are electrical field(s), and the intrabody probe comprises at least one electrode, e.g., an intrabody electrode referenced to a voltage at an external electrode. Optionally, the intrabody probe comprises a plurality of electrodes which are used to make electrical field measurements. Electrical fields may be induced from any suitable configuration of internal and/or external electrodes;

optionally including the measurement electrodes themselves. Induced field configurations are also described, for example, in relation to FIGS. 3A-3D. In embodiments wherein a plurality of electrodes are used, the electrodes may be positioned in fixed locations relative to one another (e.g., positioned along a rigid probe tip), or in a flexible relative location, for example distributed along the curvature of a lasso-like electrode probe (e.g., along the circular spine of the distal tip of a LASSO® catheter). In some embodiments, a plurality of electrodes is positioned on an expanding deployable element that distributes them around a 3-D shape such as the outline of a sphere, umbrella, ovoid, or other shape. Herein, such expanding deployable probe elements are also referred to as basket probes. In some embodiments, a basket probe comprises spaced electrodes, spaced magnetic sensors, and/or spaced sensors of another type.

A potential advantage of using larger numbers of electrodes (particularly larger numbers of more closely spaced electrodes) is a finer-grained sampling of the electrical field. Measurements from multiple electrodes can also be simultaneous, which provides a potential advantage insofar as the distance between each two electrodes can be used for analyzing the measurements obtained by the electrodes to obtain the map. For example, in some embodiments, map data are obtained by transforming sensed fields data into map data, and one or more known inter-sensor distance is used as a constraint on the transformation.

In some embodiments, information about distances between electrodes can be used in calculating features of the field such as local gradients. With deployable probes, a potential issue relates to ensuring that the relative distances among electrodes are known. In some embodiments, distances are estimated based on inter-electrode fields (e.g., distance estimate is adjusted according to a current that passes between two electrodes when activated together).

Optionally, measurements made at different times are treated as approximating measurements of the same field, as if they were taken simultaneously. Optionally, such an approximation may be accompanied with correction for changes in field measurements attributable to movement and/or drift that took place between the different times. However, using measurements taken at different times as if they were taken simultaneously may result in some loss of resolution, and there may be an advantage to putting larger weight on gradients determined from simultaneous measurements. Where a field is time-varying in structure due to external influences (e.g., movements of heartbeat and/or respiration), techniques of correction, binning, and/or gating may be applied.

Fields are a concept widely used in physics to describe conditions (for example, forces, movements, and/or energies) which distribute through space, often under the influence of field-affecting features. Such field-affecting features may include features such as, particles, charges, pressures, currents, kinetic energy, and/or mass-energy. Optionally, a field-affecting feature acts, e.g., as a source, sink, attenuator, dissipater, diffuser, deflector, absorber, phase shifter, frequency shifter, and/or concentrator. There may be any number of such field-affecting features, each having a spatially extended (perhaps theoretically infinite) range of influence. However, at any given location (e.g., a point, in a mathematical model of a field), the field is described as a single element (e.g., a scalar, vector, spinor, or tensor). The single element is understood, as applied to a physical field, to represent a physical quantity.

There is thus a kind of degeneracy in the amount of information available in a single local field measurement, insofar as it conflates the influence of multiple field-affecting features. Moreover, field influences (e.g., voltages of an electrical field induced by field-affecting features such as separated charges) may quickly attenuate in magnitude as they spread in extent, so that distant effects of individual field-affecting features are quickly overwhelmed by noise in measurement, and/or the effects of other field-affecting features. With more measurements, suitably obtained, more information about the distribution of field-affecting features may become available, at least in principle. The practical problem of using this information to reverse the conflation of field-affecting features is an aspect of what is known as the "inverse problem." Many mathematical tools are available for finding at least approximate solutions to the inverse problem; for example, the family of techniques known as iterative reconstruction algorithms (this is discussed further in relation to FIG. 5A, for example). However, there remains, for their successful application, a problem of collecting data under conditions that form a suitable starting point for such tools, given, for example, practical constraints of measurement time, measurement position, measurement noise, and/or available prior knowledge of the measurement environment.

The inventors named in the of the current application have found, surprisingly, that a medically relevant and technically available class of conditions of intrabody field measurements is serviceable to produce potentially useful images of field-affecting features within a region of a body region remote from (e.g., located at least 1 cm distance) intrabody positions at which field measurements are obtained. In embodiments, the field affecting features are within a region of a body region distanced from the intrabody positions by at least 1.5 cm, 2 cm, or 3 cm. Optionally, for example as described in relation to FIGS. 4A-4D, map production may be performed without a requirement for an explicit solution to the inverse problem.

Herein, some conditions for measurement of electrical fields and determination of field gradients using intrabody probe electrodes are described. The measurements may include, for example, impedance and/or voltage measurements, optionally as a function of electrical field phase and/or frequency. However, it should be understood that the invention is optionally applied, changed as necessary, to magnetic measurements of magnetic fields, (e.g., using coil sensors) and the determination of gradients therefrom.

In some embodiments, field measurements used to produce a map of remote field-affecting features are collected and processed as a set of measurements (optionally, a set that dynamically grows as more measurements are taken). Positions of measurements (at least relative to one another) are determined as well; recorded along with the measurements, and/or in some embodiments determined using the measurements themselves. In some embodiments, measurements are made at predetermined positions or along predetermined paths. Alternatively, measurements are obtained using whatever positions a measurement probe happens to assume. The positions may be positions which are ordinarily visited by a measurement probe during the course of a procedure (e.g., during cautious movements to find a far wall of a heart chamber). Additionally or alternatively, the positions may be chosen by an operator to particularly enhance the available detail in some region of the remote impedance map. Optionally, movement of a measurement probe between measurement positions is induced, for example, by involuntary body movements of a patient being measured; e.g., heartbeat and/or respiratory movements.

Optionally, measurements are taken at a frequency of, for example, about or at least 10 Hz, 50 Hz, 100 Hz, or 200 Hz. At a 100 Hz measurement frequency, for example, it has been found by the inventors that measurements obtained within a few seconds (e.g., about 5 seconds) of entering a new measurement region such as a heart chamber are potentially sufficient to provide an initial low-resolution map of chamber wall features such as apertures to blood vessels, valves, and/or structures such as the left atrial appendage. As sampling continues (preferably immediately; optionally after a pause), map quality generally improves, and map quality may be further enhanced by motions of the measurement probe which sample new regions and/or new orientations.

For the determination of measurement positions, any suitable measurement probe position tracking system may be used, for example, based on magnetic sensing, electrical sensing, X-ray imaging, ultrasound, and/or another positioning system. Optionally, the measurement set is obtained by measuring while moving at least one sensor (e.g., 1, 2, 3, 4, 5, 8, 10, 12, 64, 128, or 256 sensors) to different determinable positions within a sampling region. Optionally, or additionally, the measurement set is obtained by measuring from a probe which comprises a large number of sensors, for example at least 64, 128, 256, sensors; and even a single measurement from each sensor is potentially sufficient to produce an at least initial map. In some embodiments, the set of measurements is obtained from within a body lumen, for example, within a heart chamber, major blood vessel, brain ventricle, stomach, intestine, esophagus, lung, or other lumenal organ.

Image Production

At block 112, in some embodiments, a map is produced of a region remote from the positions of the measurement set, based on the measurements of the measurement set and the recorded positions of those measurements. Herein, a position of a measurement is a position of a sensor when the sensor makes the measurement, for example, a position of electrical field measurement is the position of the electrode that took the measurement when the electrode took the measurement. The map is optionally processed for presentation as an image. Optionally, the map is processed into a reconstruction of a region (e.g., using one or more additional parameters such as a separately determined width, height, depth, and/or volume of the region) which is in turn presented as an image. Examples of such images will now be presented, followed by further details of the process of the measuring, map creation, and the process of image production.

Figure 5B:
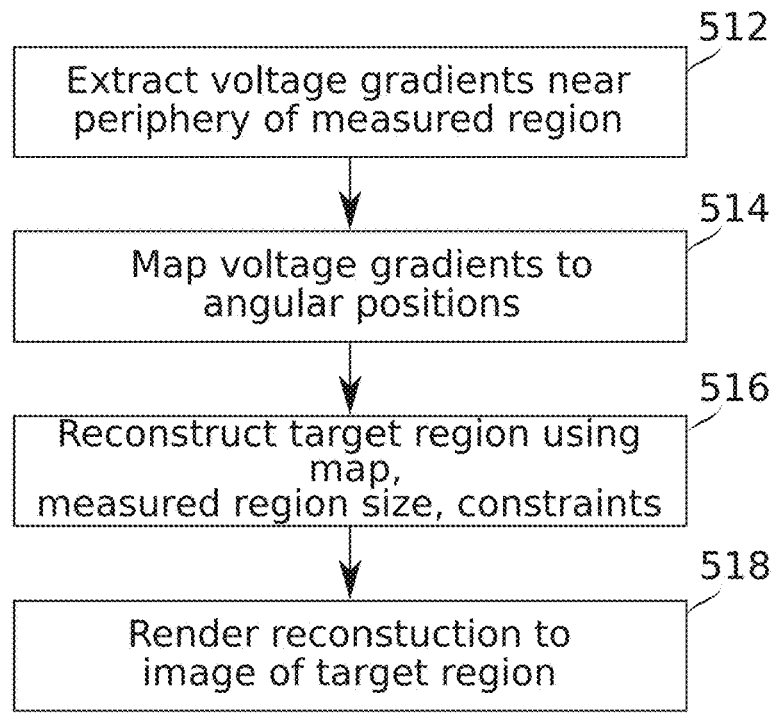
FIGS. 5B-5C are flowcharts schematically illustrating methods for producing an image of a target body region, based on of a map of anatomical structures produced using measurements from a measuring region remote from the anatomical structures of the target region, according to some embodiments of the present disclosure.

The exemplary images are presented in FIGS. 2A to 2G; details of the measurement process (e.g., of block 110) are presented at FIGS. 3A to 3D; and aspects of map, reconstruction and/or image production (e.g., of block 112) are presented in FIGS. 4A-4D, and further discussed in relation to FIGS. 5A-5B.

Example of Image Results

Figures 2A, 2B, 2C, 2D, 2E:
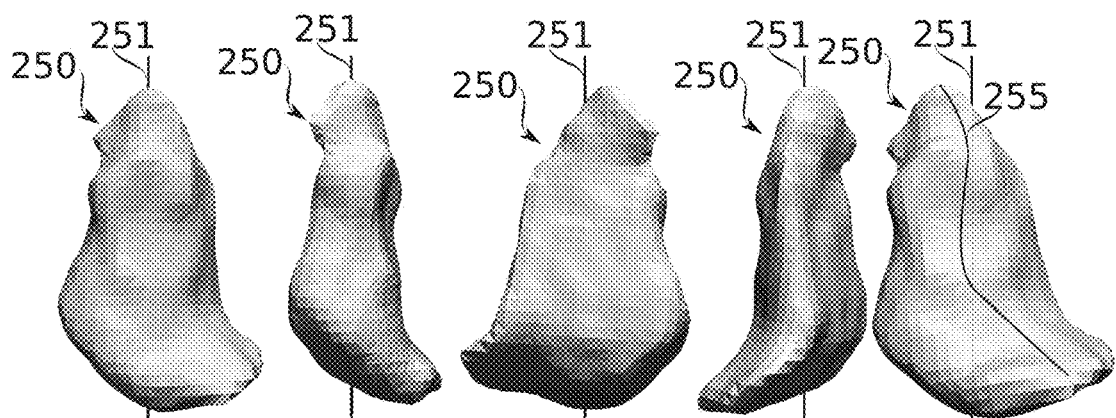
FIGS. 2A-2E show five images of a 3-D reconstruction derived from an anatomical map of an interior surface (seen from outside in "epicardial view") of a left atrium, wherein the representation is constructed using the method of FIG. 1, according to some embodiments of the present disclosure.
Figure 2F:
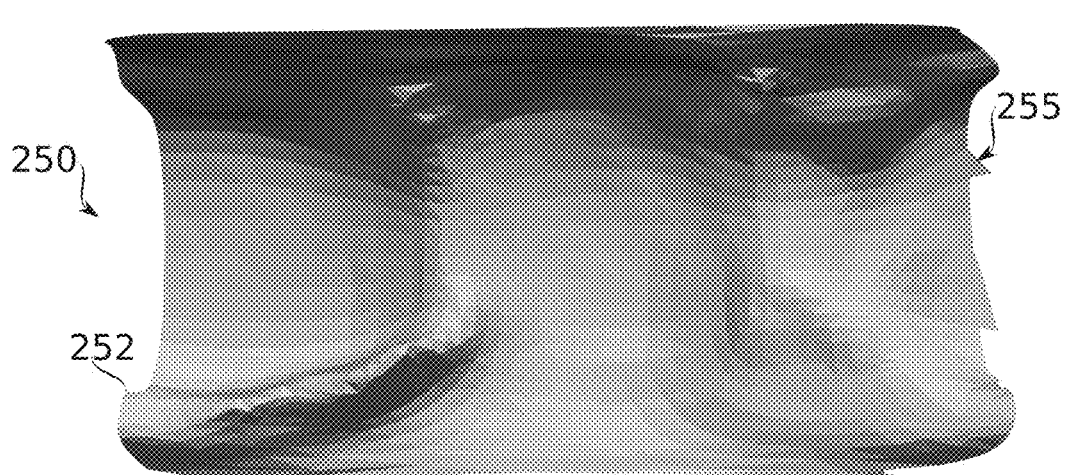
FIGS. 2F-2G illustrate two orientations ("epicardial" and "endocardial" views, respectively) of a panoramic ("unwrapped and flattened") representation of an interior surface of the left atrium of FIGS. 2A-2E, according to some embodiments of the present disclosure.
Figure 2G:
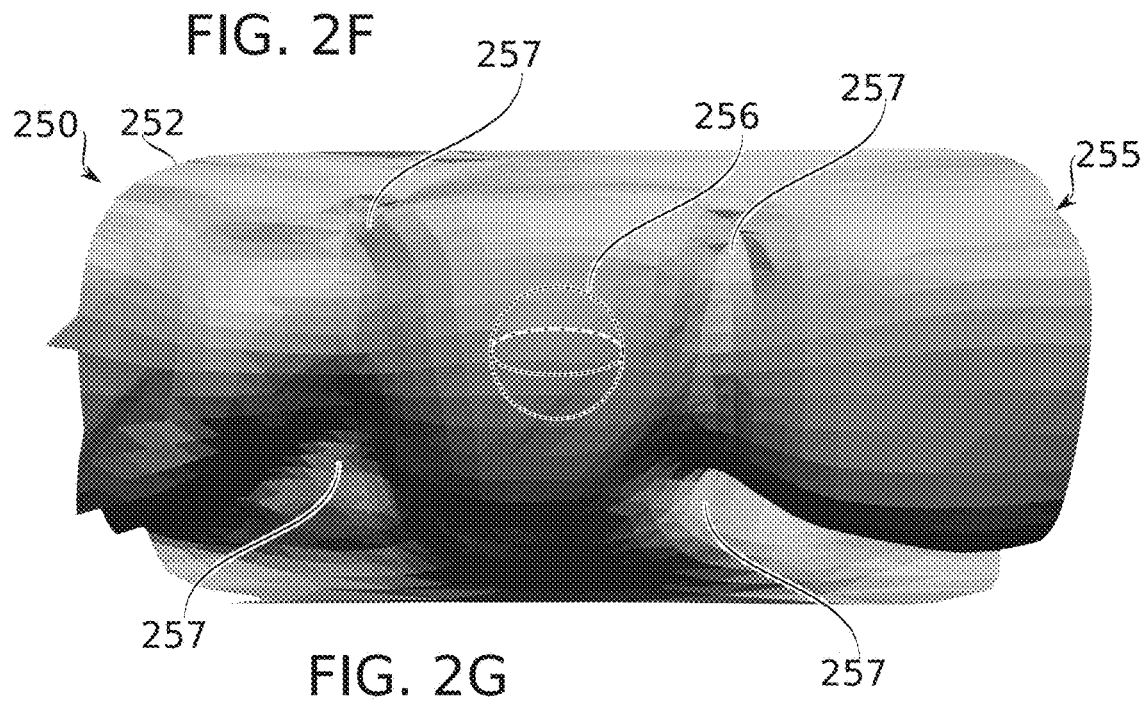

Reference is now made to FIGS. 2A-2E, which show five images of an interior surface of a left atrium, as seen from outside (epicardial view). The images have been produced from maps created using the method of FIG. 1. Each image is of a 3-D reconstruction of the outer view of the interior surface of the left atrium, reconstructed from measurements taken from within the left atrium. Reference is also made to FIGS. 2F-2G, which illustrate two images of the left atrium of FIGS. 2A-2E, according to some embodiments of the present disclosure. The images of FIGS. 2F-2G represent orientations of a panoramic view of the interior surface, as seen from outside (epicardial view, FIG. 2F) and from inside (endocardial vie, FIG. 2G). The panoramic view is obtained, in some embodiments, by "unwrapping and flattening" a reconstruction of the kind imaged in FIGS. 2A to 2E.

Figure 14:
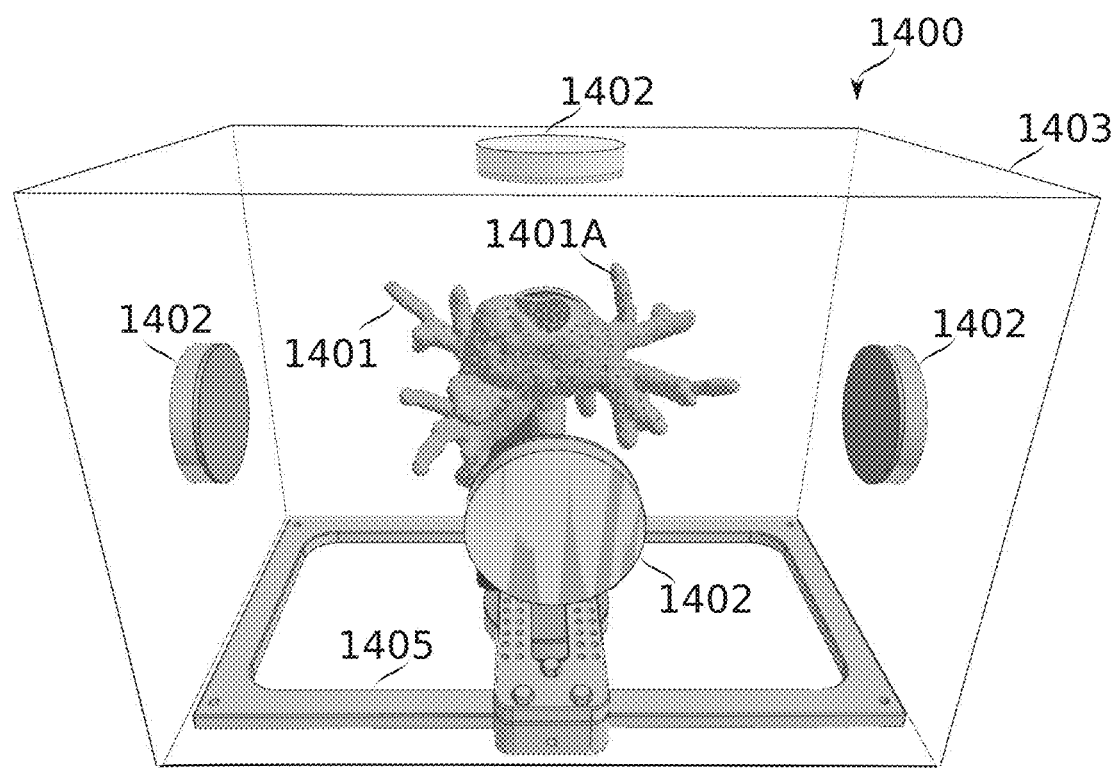
FIG. 14 schematically illustrates a measurement tank for use in electrical mapping of a polymer-based phantom left atrium, according to some embodiments of the present disclosure.
Figure 15A:
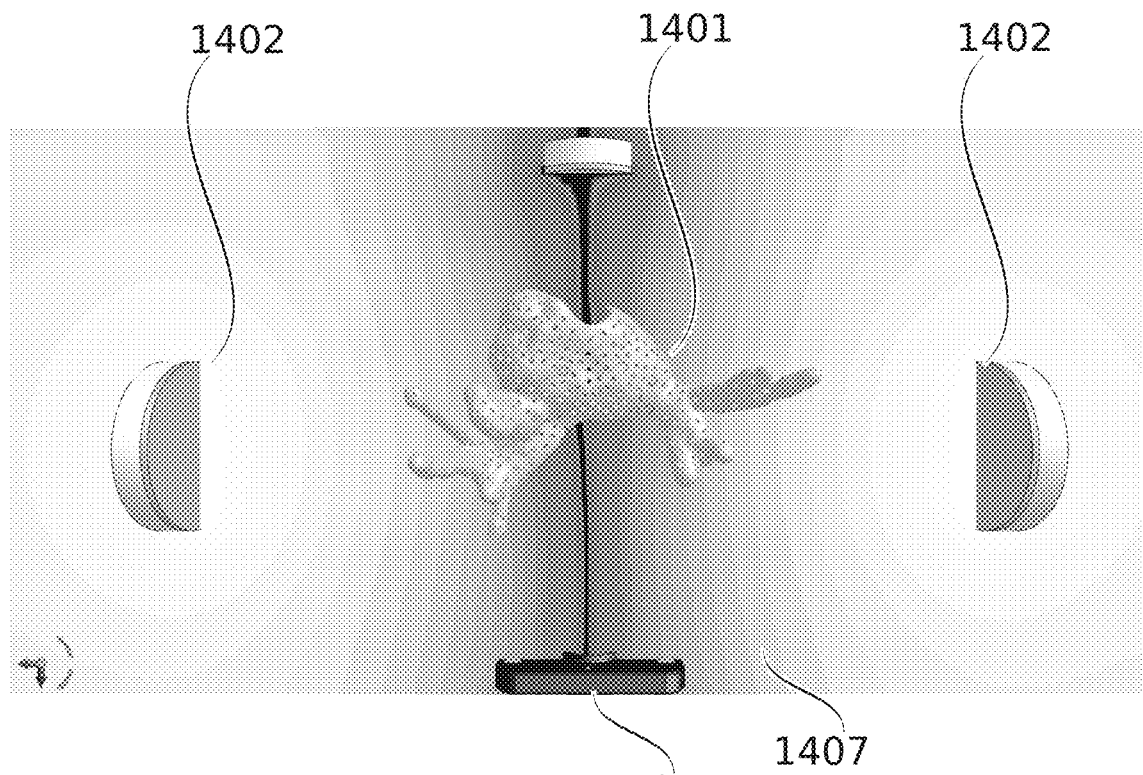
FIG. 15A shows positions of electrodes, stand, and phantom left atrium relative to electrical potential gradient of a simulated electrical field generated between two indicated electrodes, according to some embodiments of the present disclosure.
Figure 15B:
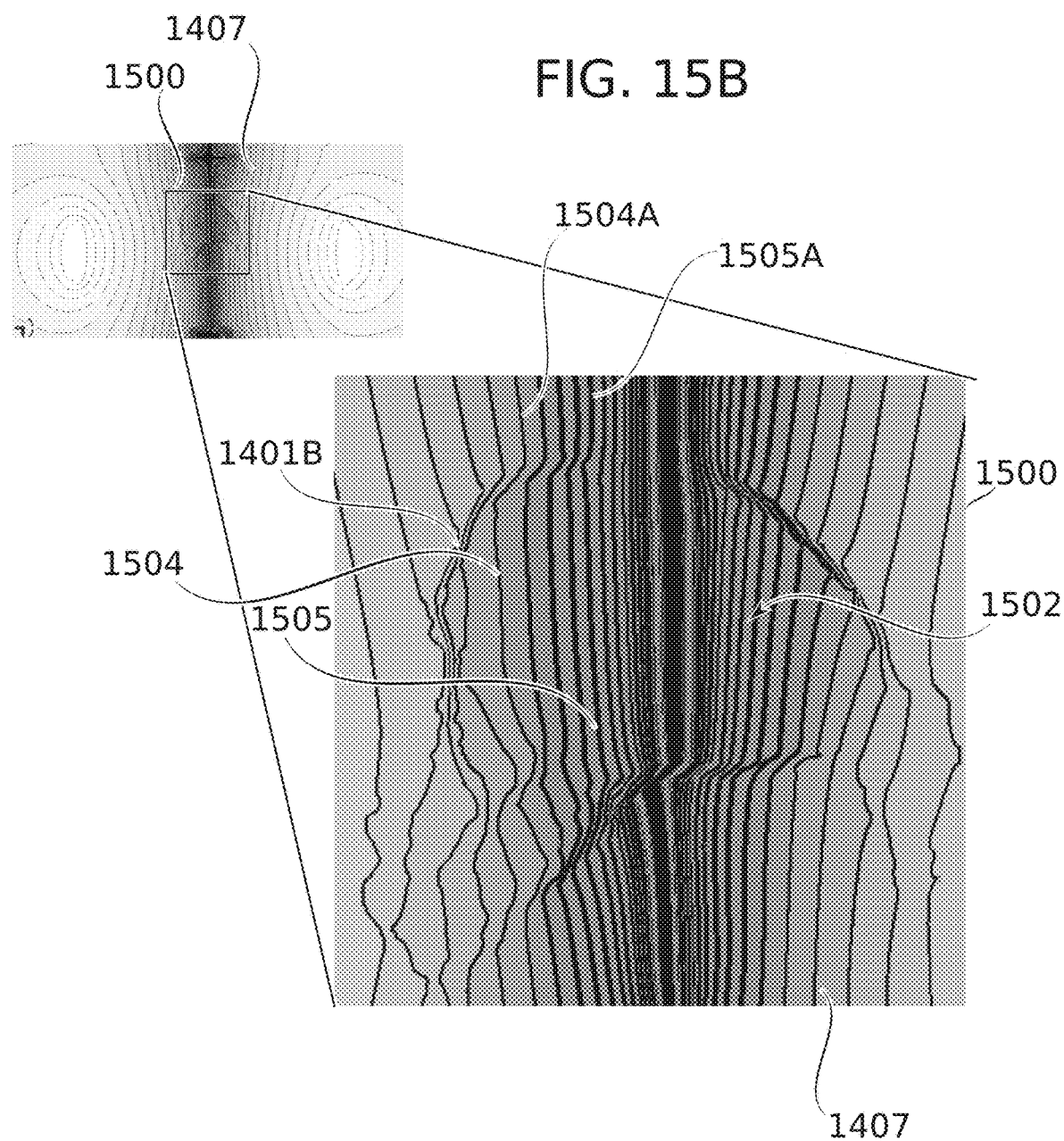
FIG. 15B illustrates the distortion of isopotential lines of the same simulated electrical field due to interaction with the heart phantom, according to some embodiments of the present disclosure.

For purposes of illustration, the images of FIGS. 2A-2G are reconstructed from voltage data measured from an electrode probe positioned within a polymer-based phantom left atrium immersed in saline (for example as described in relation to FIGS. 14-15B). Measurements were made with the electrode probe being moved only at positions remote from the wall, and concentrated in a central region symbolically indicated in FIG. 2G by sphere 256. Positioning information for the measurement electrodes was obtained by measuring voltages with respect to each of three crossed and time-varying electrical fields, and transforming these measurements to positioning information. An example of a transform which may be used in practice to obtain positioning data is provided in U.S. Provisional Patent Application No. 62/445,433 filed Jan. 12, 2017, and in International Patent Application Publication No. WO/2018/130974, but the present invention is not necessarily limited to this particular way of obtaining the positioning information.

FIGS. 2A-2E are images of the same reconstruction 250 at different rotational orientations around a vertical axis of rotation 251. In FIGS. 2F-2G, reconstruction 250 is presented as if cut open along line 255 of FIG. 2E, and spread open while maintaining the same axial orientation. FIG. 2F shows reconstruction 250 as if "from the outside", while FIG. 2G is flipped 180° end for end to display reconstruction 250 as if viewing from the inside of the lumen. Each of FIGS. 2A-2E roughly corresponds to a view from the angle of the corresponding positions of FIG. 2F immediately below it.

In some embodiments, the measurements used as inputs to create the reconstruction 250 (e.g., impedance or voltage measurements) are optionally taken from within a relatively small region (e.g., sphere 256) of the overall lumen. The amplitude of movement used for generating the views of FIGS. 2A-2G was about ±1 cm, while collecting data for about 1 min at a sampling rate of about 100 Hz. Despite this limited sampling region, features distant from sphere 256 are potentially revealed, at least in rough outline. In particular, it may be noted that the positions of the roots of the pulmonary veins 257, while not precisely outlined, are indicated by deeper indentations (visible as apparent pits from an endocardial view, and/or apparent protrusions from an epicardial view) at the positions marked. Methods of reconstruction which are able to generate images such as those presented in FIGS. 2A-2G from impedance or voltage measurements are described more particularly in relation to FIGS. 4A-4D, herein.

Reference is now made to FIG. 14, which schematically illustrates a measurement tank 1400 for use in electrical mapping of a polymer-based phantom left atrium 1401, according to some embodiments of the present disclosure. This represents, for example, a measurement tank 1400 used for measuring data described in relation to FIGS. 2A-2G. Measurements are made by moving an electrode probe around inside measurement tank 1400, and particular inside of the phantom left atrium 1401.

Tank 1400 comprises walls 1403 made, e.g., of glass, and which are made watertight to allow filling with saline (in simulation of the electrical properties of blood). Electrodes 1402 are configured to transmit electrical fields between them (e.g., between oppositely positioned pairs of electrodes 1402) through the saline and through polymer-based phantom left atrium 1401. In some embodiments, these are the electrical fields which are measured during movements of the electrode probe. To approximate electrical conductivity properties of heart tissue, the polymer material of left atrium 1401 is optionally punctured by an array of small holes 1401A (illustrated in FIG. 14 as stippling on the surface of phantom left atrium 1401). Stand 1405 supports phantom left atrium 1401 near the center of tank 1400.

Reference is now made to FIG. 15A, which shows positions of electrodes 1402, stand 1405, and phantom left atrium 1401 relative to electrical potential gradient of a simulated electrical field 1407 generated between two indicated electrodes 1402, according to some embodiments of the present disclosure. Reference is also made to FIG. 15B, which illustrates the distortion of isopotential lines of the same simulated electrical field 1407 due to interaction with the heart phantom 1401, according to some embodiments of the present disclosure.

Region 1500 of FIG. 15B is shown expanded in the inset view. Region 1502 corresponds to a cross-section through the central lumen of phantom 1401. Across the thickness 1401B which corresponds to the wall of phantom 1401, isopotential lines of electrical field 1407 are displaced. What may be noted is that isopotential lines (e.g., isopotential line 1504) near thickness 1401B are displaced somewhat more than isopotential lines (e.g., isopotential line 1505) which are more central. The amount of distortion can be approximately judged by comparing the horizontal position of relatively undistorted isopotential line portions 1504A, 1505A to the horizontal positions of corresponding isopotential lines 1504, 1505. Although there is apparently less gradient distortion more centrally, the wall-induced distortion still creates there an imprint on the electrical field's gradient. In some embodiments of the present invention, this distortion is used for creating images of tissue structures remote from the region at which electrical field measurements were performed.

Figure 3A:
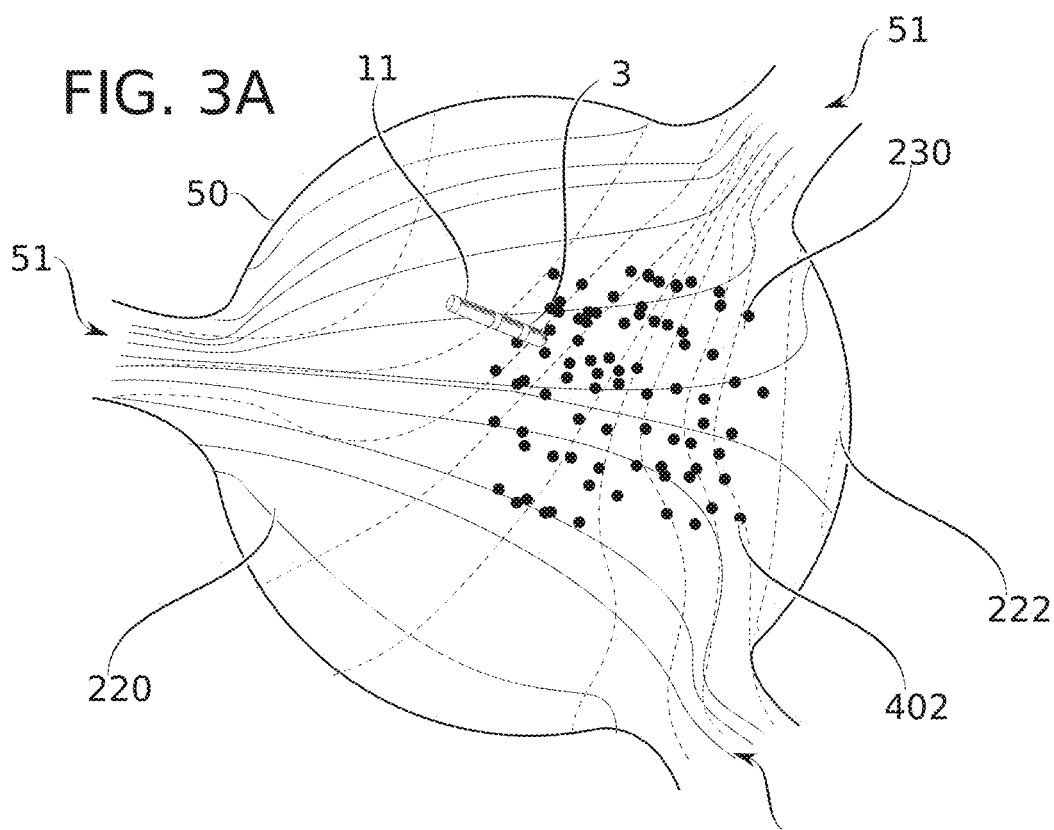
FIG. 3A schematically illustrates a set of measurement positions shown relative to a body region and relative to induced fields extending throughout the body region and induced from outside the body region, according to some embodiments of the present disclosure.

Measurements and Measurement Conditions
Measurements of Fields Generated from Outside the Region to be Imaged Reference is now made to FIG. 3A, which schematically illustrates a set 402 of measurement positions shown relative to a body region 50 and relative to induced fields extending throughout the body region 50 and induced (transmitted) from electrodes located outside the body region, according to some embodiments of the present disclosure. In some embodiments, the inducing electrodes are positioned outside of the body itself, optionally as body surface electrodes. In some embodiments, the transmitting electrical field electrodes are within the body but outside the region to be imaged; for example, positioned in a coronary sinus when the area to be imaged is left coronary atrium. Example fields are shown in the figure as field lines, wherein one field is shown with solid lines (field 220), and the other with dashed lines (field 222).

For simplicity of illustration, body region 50 and associated features are drawn as two-dimensional; however it is to be understood that the structures involved are three-dimensional body portions.

In some embodiments, a measurement set 402 is obtained by moving an electrode probe 11 around within a relatively restricted first region of the anatomy while making measurements (e.g., impedance and/or voltage measurements) using one or more probe electrodes 3. The electrical fields 220, 222 of FIG. 3A are shown in a mutually crossing configuration (in a full 3-D example, there are optionally one or more additional electrical fields, for example, at least three crossing electrical fields, including a field extending into the plane of the figure). Each field line may be understood as indicating an amount of electrical flux (current) passing generally along it, so that closer-spaced field lines correspond to a condition of higher local flux than wider-spaced lines. In the example of FIG. 3A, electrical fields are generated externally to body region 50. For example, they may be generated from body-external electrodes such as body surface electrodes. Additionally or alternatively, they may be generated from body-internal electrodes, e.g., electrodes placed within a body region external to body region 50. For example, if body region 50 is a left atrium, then electrical fields 220, 222 may be generated from catheter electrodes placed in another body lumen such as an esophagus, coronary sinus or other blood vessel, and/or an adjacent heart chamber.

As shown in FIG. 3A, courses of the field lines (solid and dotted field lines are shown corresponding to the two fields 220, 222) are significantly affected by lumens 51 leading away from the central chamber. In the example shown, field lines tend to concentrate near openings of lumens more than in other regions. This change in field line concentrations may be referred to as distortion, e.g., in comparison to non-distorted field line concentrations expected in absence of any field-affecting features such as lumens 51. As used herein, the term "distortion" refers to differences between measurements obtained in the presence of field-affecting features, and measurements expected to be obtained in absence of those field affecting features. In some embodiments, the measurement expected to be obtained in absence of field affecting features is approximated by a reference value, which in some embodiments may have the same value for all directions. When the measurements are of a vector quantity, such as a field, field gradient, voltage gradient, or the like, the distortion may also be a vector, and may be referred to as a distortion vector. The concentration of field lines may be understood as a consequence of relatively low resistance of lumens 51 allowing the passage of higher currents, compared to nearby structures (the lumenal wall of body region 50) which are relatively insulating and resistant to the passage of current. The relative concentration of field lines is accompanied by changes in certain measurements of a time-varying field, in particular voltages, phases (e.g., components of complex impedances). Insofar as impedances of different tissue types vary as a function of frequency, the field distortion itself may be different at different frequencies.

Positions of probe 11 during measurement of measurement set 402 are recorded by any suitable means, for example, ultrasound mapping, X-ray radiography, a magnetic positioning system wherein positions are determined based on measurements of induced magnetic fields, and/or an impedance positioning system, wherein positions are determined based on measurements of induced electrical fields. Optionally, gating is performed based on heartbeat and/or respiration phase.

It is noted that the relatively restricted first region of the anatomy in which the measurement set 402 is obtained is shown as significantly smaller than the containing second region of the anatomy which comprises the wall of body region 50 and its connecting lumens 51. For example, a volume enclosing the positions of the measurement set is optionally less than 50%, 25%, 15%, and/or 10%, of the volume of body region 50. In some embodiments, the volume of the measurement set may be defined as a volume enclosed by a convex shell containing the positions of at least 80% of all the measurement set members. Optionally, the volume is defined with respect to positions of all the measurement set members measured within a certain brief interval of time (e.g., less than 5 seconds, 10 seconds, and/or 30 seconds), and which are used to produce an at least initial map, and/or a reconstruction and/or image based on the map.

In some embodiments, an early map, and/or a reconstruction and/or image based on the early map, is generated based on measurements obtained within a brief interval of time (e.g., less than 5 seconds, 10 seconds, 20 seconds, and/or 30 seconds). Also for example, the time is no more than is used to obtain less than 500 measurements, 1000 measurements, 2000 measurements, and/or 3000 measurements. In some embodiments, regardless of relative volume to the second region, the first region of anatomy (at least in its size measured for generation of the early map) is defined as the smallest contiguous and convex volume containing positions of the measurements obtained during the brief interval of time. Optionally, the first region is no more than 10%, 20%, 30%, 40%, or 50% larger in volume than the smallest contiguous and convex volume. In some embodiments, the early map includes representations including at least about a quarter, half, and optionally all of a spherical solid angle around a position within the first region of the anatomy.

It is noted that these interval of times are potentially not enough to exhaustively explore a region to be mapped Yet, they may provide enough information to be useful in providing a physician navigating a catheter in the region at least a minimal degree of orientation. In some embodiments, the measuring of measurements used in producing a map occurs immediately upon navigation of a sensor into a new position.

Optionally, at least one indicating feature of an initial map, and/or a later map corresponds to an anatomical structure in the target region. Each such anatomical structure in the target region is optionally positioned at least 1 cm, 1.5 cm, 2 cm, 3 cm, or more away from each corresponding position of at which measurements of the indicating feature were taken to create the map. Examples of indicating features include features that indicate one or more of the position of the anatomical structure in the target region, the state of tissue of the anatomical structure (for example: healthy, edemic, or fibrotic), and/or the type of tissue (for example, cardiac muscle, connective tissue, lung tissue, bone or cartilage) of the anatomical structure. In some embodiments, the first region is remote from the features of the wall and its openings; for example, at least 50% of the features which are to be mapped in the second, target region of the body are no closer to the positions of the measurement set 402 than 1 cm, 1.5 cm, 2 cm, 3 cm, or another larger, or intermediate distance. Additionally or alternatively, the target region is at least a distance of 1 cm, 1.5 cm, 2 cm, or 3 cm from a minimum convex shell containing at least 80% of all the measurement set points in the measurement region used in the mapping.

Nevertheless, despite the remoteness of the measurement region from the target region, the fields sensed in the measurement region are influenced by the target region, so that the target region may be mapped without being visited. For example, in FIG. 3A, measurement set 402 may be influenced by, and therefore be informative of, electrical field concentrations occurring at the lumens, as indications of these field concentrations propagate along the field lines into the region of the measurement set 402. Use of this information to form a map of the target region is discussed further in relation to FIGS. 4A-4D, herein.

Measurements of Fields Generated Inside the Region to be Imaged

Figure 3B:
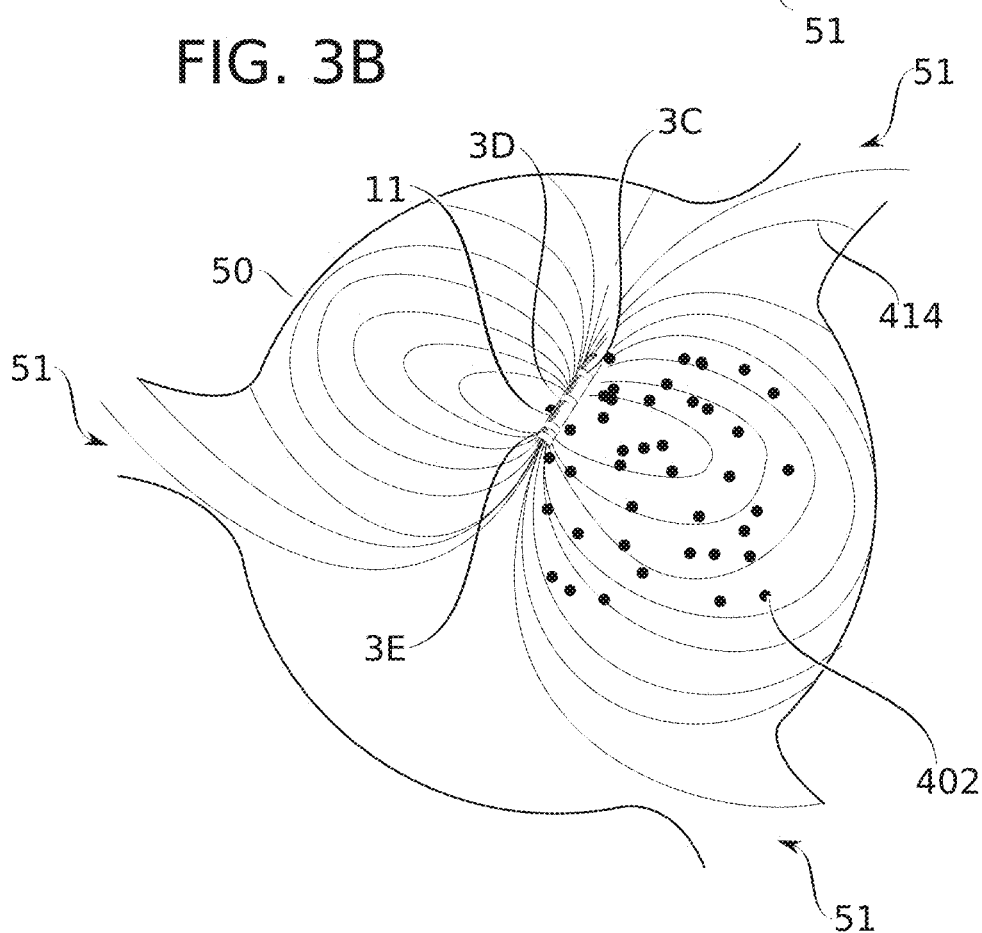
FIG. 3B schematically illustrates a set of measurement positions shown relative to a body region and relative to induced fields extending throughout the body region and induced from electrodes of the measurement probe itself, according to some embodiments of the present disclosure.

Reference is now made to FIG. 3B, which schematically illustrates a set of measurement positions shown relative to a body region and relative to induced fields extending throughout the body region and induced from a plurality of electrodes of the measurement probe 11 itself, according to some embodiments of the present disclosure. Further reference is made to FIGS. 3C-3D, which schematically illustrate a set of measurement positions shown relative to a body region and relative to induced fields extending throughout the body region and induced from the measurement probe 11 itself, according to some embodiments of the present disclosure.

Figure 3C:
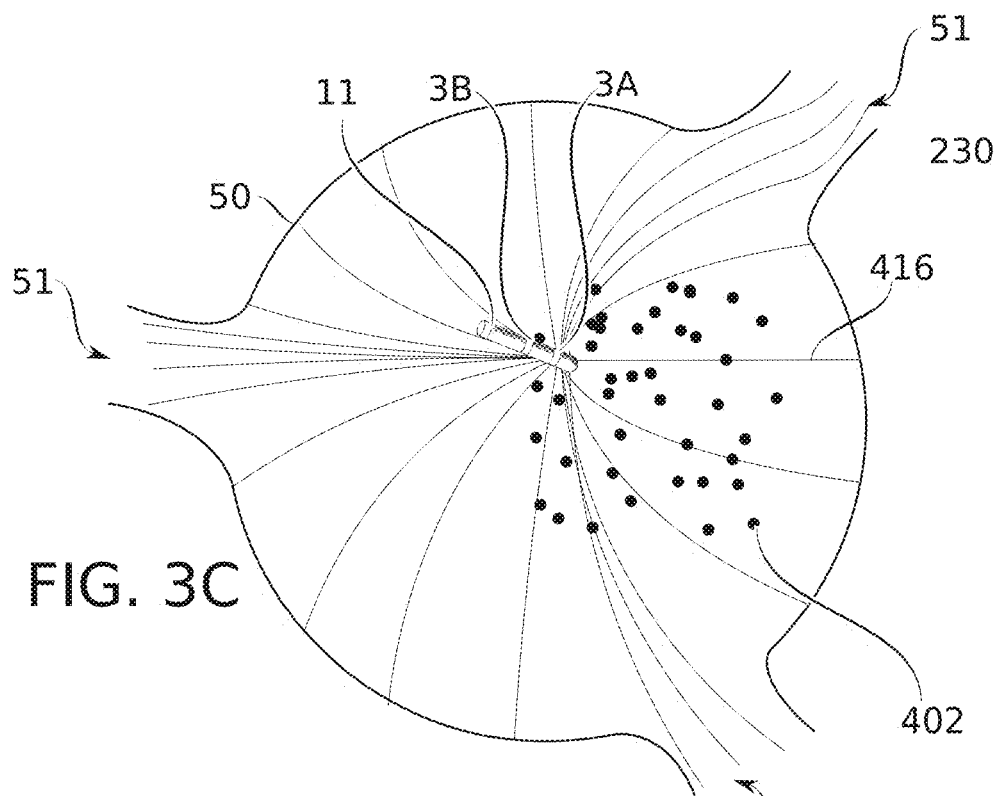
FIGS. 3C-3D schematically illustrate a set of measurement positions shown relative to a body region and relative to induced fields extending throughout the body region and induced from the measurement probe itself, according to some embodiments of the present disclosure.
Figure 3D:
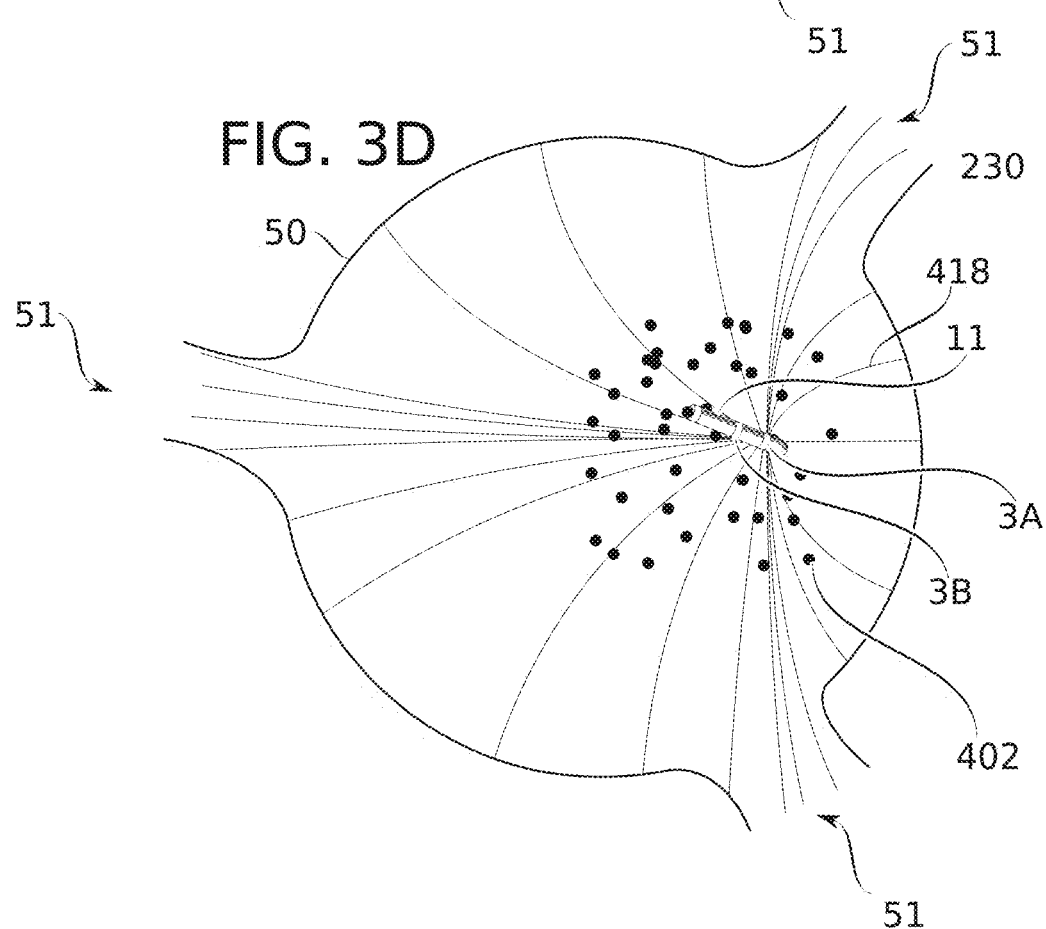

In some embodiments of the invention a same electrode probe 11 is used to induce electrical fields and to measure the induced electrical fields. FIG. 3B shows an example of a field induced from a pair of electrodes 3D, 3E being operated in bipolar mode, and distorted by field-affecting features such as lumens 51. Field characteristics of electrical field 414 sensed at electrode 3C vary with the position (i.e. center position and/or orientation) of probe 11. Examples of field characteristics may include voltage, phase, and/or impedance. FIGS. 3C-3D show examples of distortions and changes in distortions in fields induced from an electrode 3A being operated in monopolar mode (e.g., paired with an external grounding electrode at a distance of several centimeters (e.g., 5 or more centimeters) from the intrabody position of the probe 11). In FIG. 3C, the field 416 induced from electrode 3A spreads throughout a cavity defined by body region 50, but is concentrated by the regions of lower resistance represented by lumens 51 (e.g., corresponding to body region 50 being a left atrium, and lumens 51 being pulmonary veins). In FIG. 3D, another field shape is induced while probe 11 occupies a different position.

Any one of the electrodes on probe 11 (e.g., electrode 3B) potentially senses a slightly different electrical field, depending on its position nearby field inducing electrode 3A. Similarly, if there is another catheter probe within the cavity of body region 50, each one of the electrodes on this other catheter probe potentially senses a slightly different electrical field. What is sensed and measured by a measuring electrode depends on how surrounding structures affect the overall shape of the field, and particularly on how the surrounding structures affect the field in the vicinity of the measuring electrode. Monopolar induction from a single electrode is shown for purposes of description; but optionally, there is a plurality of electrical fields generated from different electrodes of probe 11 (in one or both of monopolar and bipolar mode) simultaneously (e.g., at different frequencies) and/or in any suitable order of pulsed operation, each field oriented in a different direction from the others. Thus, at a single position of probe 11, there is optionally simultaneous sensing of electrical field parameters in a plurality of different directions from probe 11.

In some embodiments, the same fields (e.g., electrical fields) are used for sensing of both position and effects of field-affecting features—field distortions—for example, in any of the field configurations discussed in relation to FIGS. 3A-3D.

To a significant extent, electrical field distortions may themselves be a cause of spatial positioning inaccuracies when using impedance positioning. For example, extracting position information from impedance measurements, while assuming that field distortions are negligible, may cause large errors in the obtained positions. Thus, there is potentially a synergy between distortion-correcting positioning techniques and field distortion-based mapping. In a particular example of this, U.S. Provisional Patent Application No. 62/445,433 filed Jan. 12, 2017 (the contents of which are included herein by reference in their entirety) describes the use of known distances between electrodes on a multielectrode probe as a kind of ruler, allowing spatial calibration of voltage gradients for assistance in navigation and/or reconstruction of a space. In some embodiments, the same or a similar method can be used to assess field distortions; as described in the following examples:

In a first example: measurements taken simultaneously by a plurality of electrodes of the same electrode probe provide a direct indication of local electrical field gradient (difference between voltages at each electrode divided by the distance between them), with new field gradient measurements optionally being obtained at each new position of the electrode probe. These gradients are directly an indication of relative electrical field line (flux) concentration and/or dispersion.

In a second example: with enough separate measurements (e.g., at least 500, 1000, 2000 or more measurements), and using a method of estimating spatial positions of measurements such as that described in U.S. Provisional Patent Application No. 62/445,433 filed Jan. 12, 2017; voltage measurements can also be related to one another across positions that were measured at different times, with the electrode probe itself in different positions. In some embodiments, the method of reconstruction of the measurement space is based on measurements from a plurality of sensors (e.g., an intrabody probe carrying a plurality of sensors such as electrodes occupying known spaced positions relative to the geometry of the intrabody probe). In some embodiments, the reconstruction process is guided by known spatial constraints on the relative positions of the plurality of sensors. Optionally, local spatial calibration defined by the spatial constraints is used in combination with constraints on the spatial coherence of measurements as part of the reconstruction process.

The measurements are of one or more parameters treated singly or in combination as identifying of particular locations within the body cavity for purposes of reconstruction. Optionally, the parameters are treated as being identifiers of particular locations under particular conditions, for example as discussed herein in relation to variation in state over time (phasic state variation, for example). In some embodiments, the measurements comprise measurements of voltages within crossed, time-varying electromagnetic fields. To distinguish the fields, in some embodiments, the crossed electromagnetic fields vary at distinguishable frequencies. As used herein, crossed or crossing fields are fields directed in directions that are not parallel to each other, nor anti-parallel, so that the direction of each field crosses the directions of all the other fields. Crossing fields may allow assigning to each point in space a unique combination of field values, provided the number of the crossing fields is not smaller than the dimensionality of the space. Thus, for unambiguously mapping a three dimensional space, at least three crossing fields are used, and more may be used. A larger number of crossing fields may provide information usable, for example, for noise reduction and improvement of robustness in comparison to robustness achievable with only three crossing fields. The voltage gradients of the crossed electromagnetic fields are used, in some embodiments, to define axes indicating spatial position as a function of measured voltage. Since the voltage gradients are ordinarily curved, and/or otherwise irregular, the conversion to axis-defined position generally relies on the use of some form of transformation, which is itself potentially non-linear, dynamic, and/or subject to errors in estimation and/or calibration.

In some embodiments, reconstruction of a body cavity region and/or navigation in a body cavity using the reconstruction may be obtained by calculating a transform function $T(x)$ on set of measurements X to obtain R, e.g., a reconstruction of where those measurements are located in a body cavity. Measurements X may comprise measurements taken from a plurality of different electrodes mounted on a probe moved within the body cavity. A transform function $T(x)$ may be calculated such that $T(X) \rightarrow R$. In some embodiments, a pre-acquired image and/or other data of the body cavity may be available, e.g., a CT image of the body cavity, and used for the reconstruction and/or navigation in the body cavity. For example, it may be used for calculating the transform function, such that $T(X) \rightarrow R$ (R being constrained by dimensions of the body cavity in the CT image).

In some embodiments an inverse transformation of T ($T^{-1}$) is determined (e.g., from T), such that $T^{-1}(R) \rightarrow V$. The inverse transform result V recovers (at least approximately) voltages of measurements X, but also estimates of other voltages in position that may not have been directly measured from originally. From V, the local derivative of V in R, ($\partial V / \partial R$) may be determined.

Construction of an Image from Measurements
Angular Projection Method

Reference is now made to FIGS. 4A-4D, which schematically illustrate the conversion of measurement results (obtained, for example, as shown in FIGS. 3A-3D) into a representation (e.g., an image) of a body region 50, according to some embodiments of the present disclosure.

In FIG. 4A, flux lines of electrical fields 220, 222 are shown crossing within body region 50, including field concentrations at lumens 51, as described for FIG. 3A. Measurements (not shown) have been taken in the same general region as measurements 402 of FIG. 3A.

Circle 235 represents both (1) an optional general position of a shell boundary along which measurements 402 are selected for use in forming a mapped representation of body region 50, and (2) a reference electrical field gradient magnitude (e.g., expressed in mV/cm) for a circular graph. The reference magnitude is chosen in this example to be the lowest gradient measured around the shell (but can be any reference magnitude in principle). The distance of curve 230 from circle 235 (considered as a reference gradient magnitude) represents electrical field gradient magnitude and/or flux density as a function of angular position around the shell also represented by circle 235.

Comparing FIGS. 4B and 4C (which show different portions of the elements of FIG. 4A), it may be observed that the three lobes 230A, 230B, 230C correspond roughly to the positions of the three lumens 51 leading off of the cavity defined by body region 50. Finally, further illustrating the general correspondence, FIG. 4D converts the features of FIGS. 4B and 4C to a combined polar plot which overlays negative amplitude (−r) of curve 230 with radial distance D of body region 50 (including lumens 51) from its center, each plotted as a function of angle θ. Such a plot may be understood as indicating an "unwrapped" analogue for a 2-D space of the 3-D panoramic plot, e.g., of FIG. 2G.

When only a limited set of measurements is used for plotting the plot of FIG. 4D (e.g., a set of measurements obtained in the first 5 seconds of measuring), the FIG. 4D represents structures of body region 50 with less detail, compared to the level of details available with a more developed set of measurements (e.g., obtained during a whole minute of measuring). Nevertheless, even a limited set of measurements potentially provides enough detail to provide a useful early indication to a user of where, relative to the position of a measurement probe, there may be found certain landmarks of interest (e.g., "topographical landmarks") within a body region 50.

The above-described method treats field distortions at each angular position as being apparently due to an angularly isolated field-affecting feature (topographical structure, for example). However, a variant of the method is potentially useful for distinguishing closer and more distance features, using the assumption that more distant features cause distortions that diminish more slowly with distance from the feature causing them. So, broadly speaking, a total distortion associated with a particular angular direction (e.g., because it decreases moving further away from that direction) can potentially be decomposed into a fast-diminishing component and a slow-diminishing component, wherein the slow-diminishing component is due to a further-away source of distortion.

Moreover, an initial map can be refined in different ways upon the acquisition of further data, for example as described in relation to FIGS. 6-11D herein.

Displacement Map—Electrical Field Gradient Features and Behaviors in a Left Atrium Reference is now made to FIG. 5A, which schematically illustrates an example of the spatial distribution of electrical field gradient magnitudes and directions in a heart chamber, according to some embodiments of the present disclosure. Reference is also made to FIGS. 11A-11D, which schematically illustrate topographical features of a left atrium, according to some embodiments of the present disclosure.

FIG. 5A illustrates, using a plurality of arrows 201, representing electrical field gradient distortion vectors, which in the case of FIG. 5A is the magnitude and direction of differences between the electrical field gradient measured within a left atrium 40, and a reference electrical field gradient (e.g., 10 mV/cm).

Optionally, the reference gradient is chosen based on the measurement data itself (e.g., an average value within selected region). Optionally, the reference gradient is non-constant; for example, based on a model of electrical field behavior for a particular set of field parameters (e.g., electrode configurations, electrode driving parameters, and/or dielectric properties of an idealized transmission medium) in the absence of the particular field-affecting features of interest. Voltage gradients tend to be steeper in regions near borders between materials having substantially different conductivity, such as the border between a blood vessel or cardiac chamber wall and the blood within it. Gradient decay can be exponentially rapid near such a boundary, for example, proportional to a power of five of distance from the boundary.

FIG. 5A is also referred to herein as a displacement map. The arrows 201 may be considered to represent displacements from a certain reference arrangement of electrical field isopotential lines, and/or to represent distortions in the estimated size of a multi-electrode measurement probe which would result from assuming some particular reference electrical field gradient, compared to the known actual size of the probe.

Figure 11A:
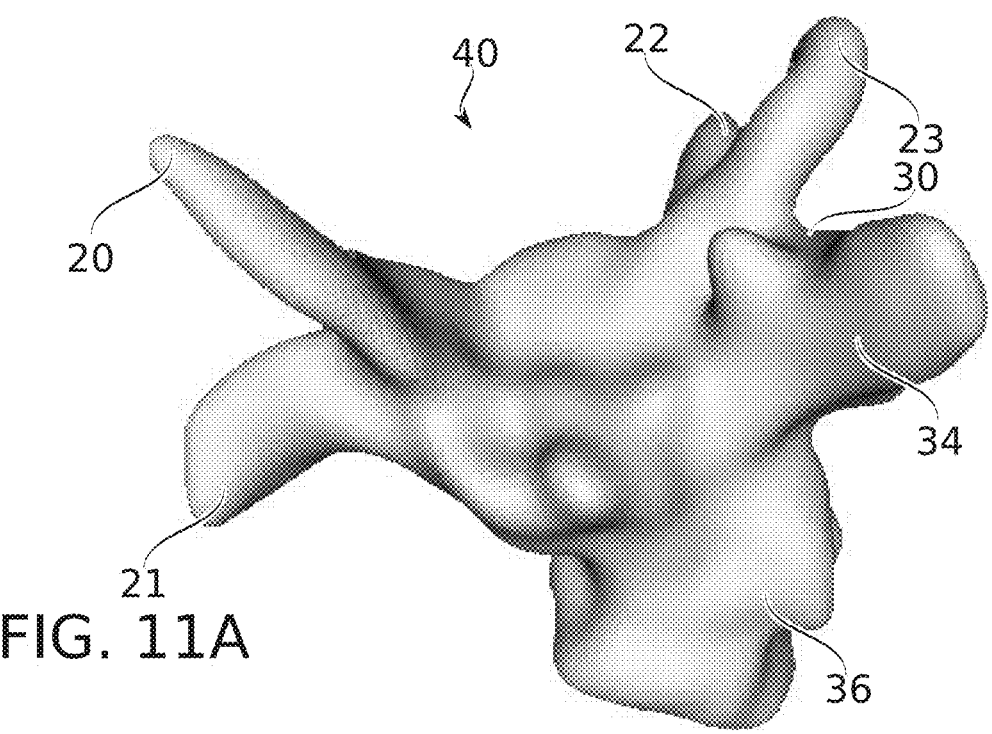
FIGS. 11A-11B schematically illustrate topographical features of a left atrium, according to some embodiments of the present disclosure.
Figure 11B:
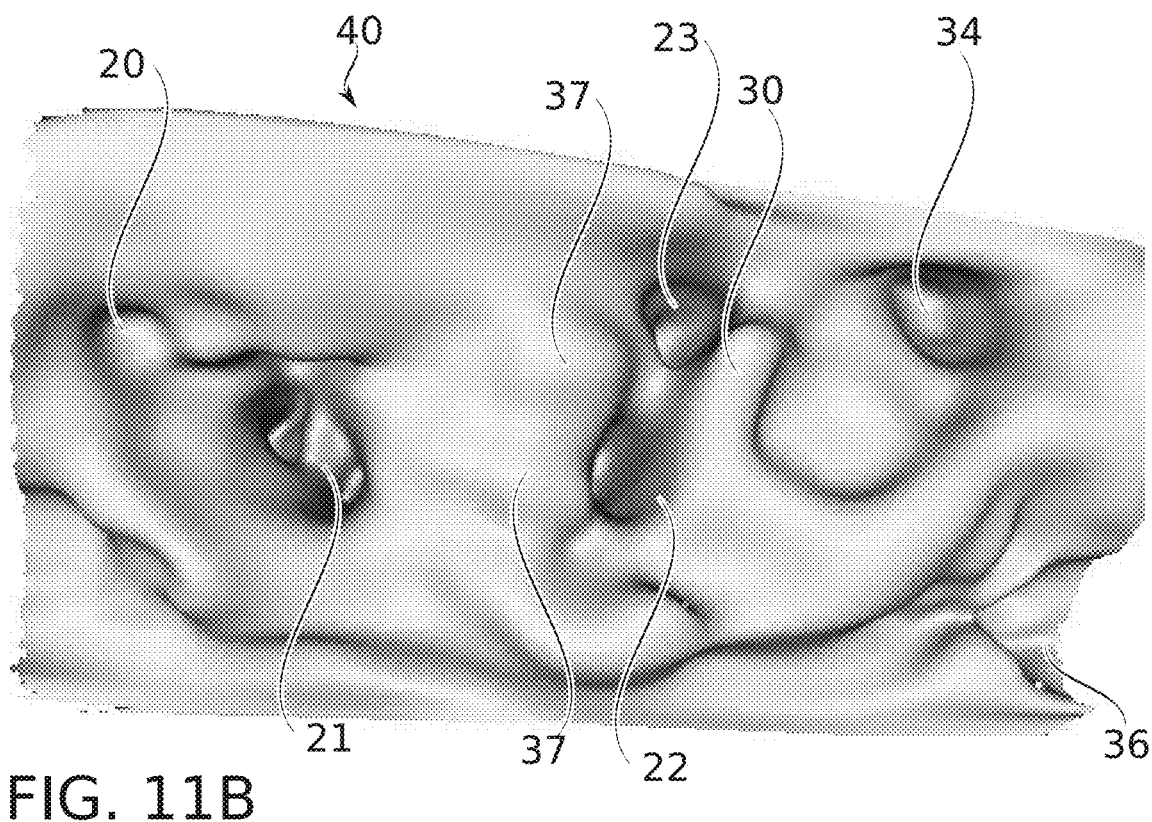
Figure 11C:
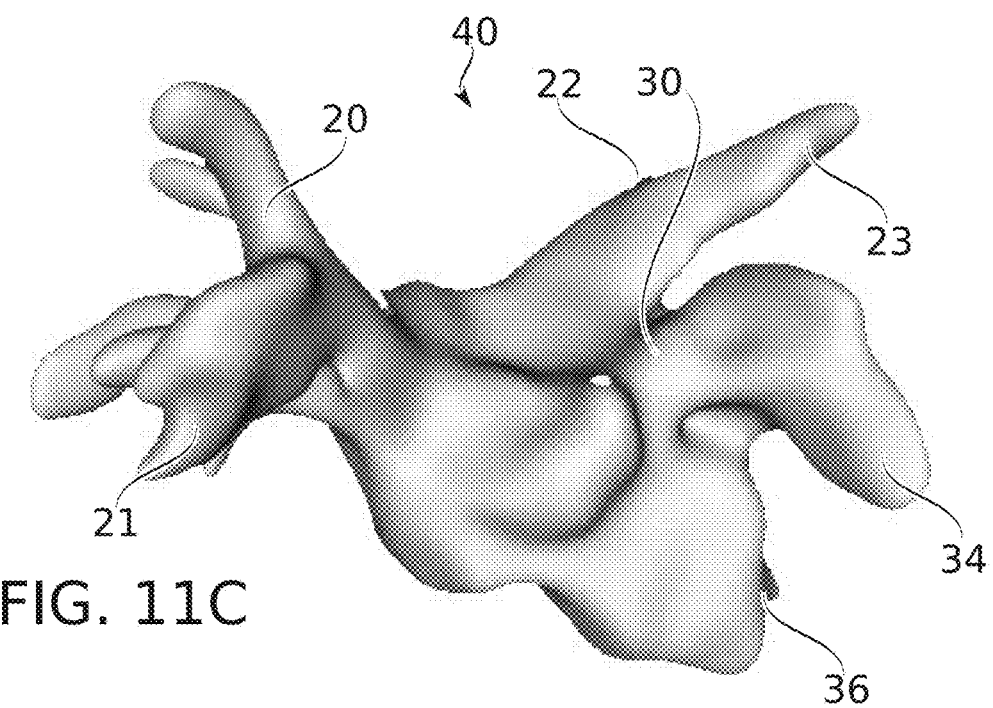
FIGS. 11C-11D schematically illustrate topographical features of a left atrium, according to some embodiments of the present disclosure.
Figure 11D:
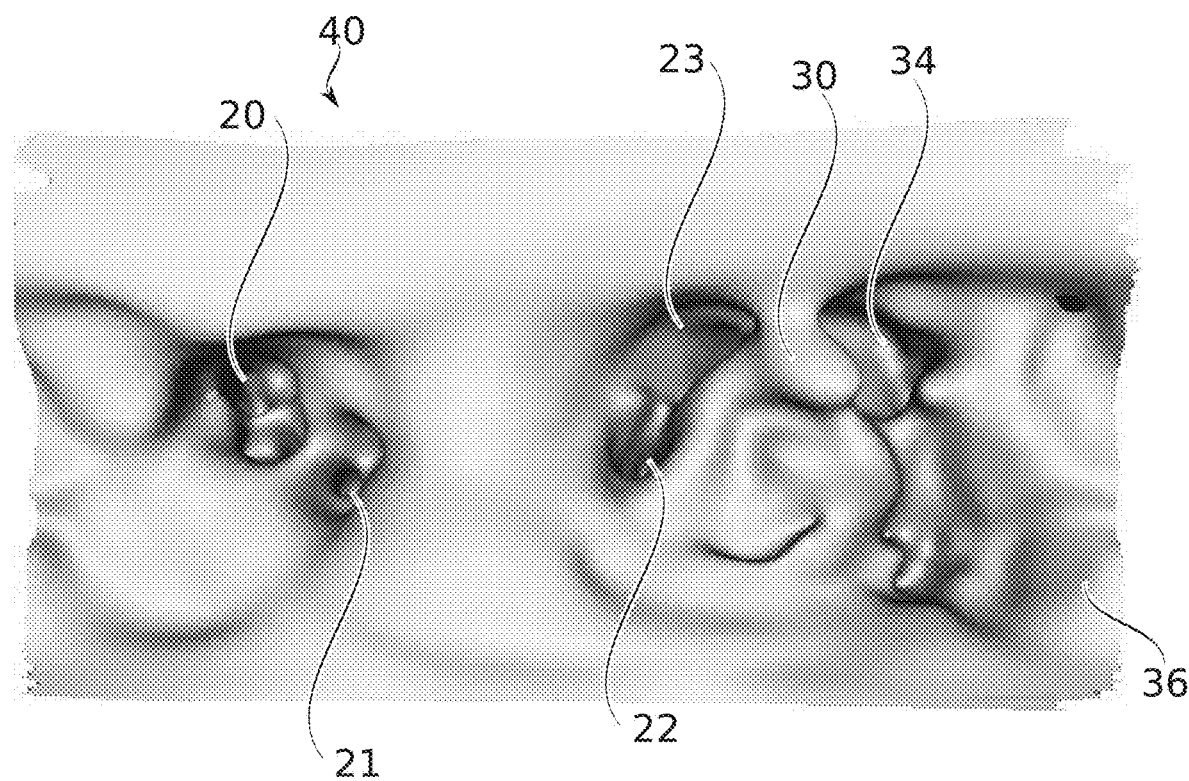

For reference in view of features mentioned in the descriptions to follow, FIGS. 11A-11D show detailed anatomical representations of the interior surface of a left atrium 40, each obtained in part by remote impedance mapping (using the remote impedance mapping method, e.g., of FIG. 1), and in part by measurements made by a measurement probe while close to and/or in contact with features of the left atrium 40 shown. FIGS. 11A and 11C are images of reconstructions of the inner surface of different left atria as viewed from outside the atrium ("epicardial view"), based on a map using remote field gradient mapping supplemented by measurements from closer to the atrial and/or blood vessel walls. FIGS. 11B and 11D comprise panoramic views of the corresponding left atria, as viewed from within ("endocardial view"); constructed, from a reconstruction, for example, as described in relation to FIGS. 2F-2G herein.

FIGS. 11A-11D each show four pulmonary veins (PV) 257 (indicated collectively in FIG. 2G), including the right superior PV 20 (RSPV), the right inferior PV 21 (RIPV), the left superior PV 23 (LSPV), and the left inferior PV 22 (LIPV). They also indicate the left atrial appendage 34, and the position of the mitral valve 36. Also indicated is the position of the left atrial appendage (LAA) ridge 30 (sometimes called the "coumadin" or "warfarin" ridge 30; because where prominent, LAA ridge 30 is sometimes confused with a blood clot associated with the LAA, leading to unnecessary anticoagulant treatment).

The measurements used in creating FIG. 5A were of a plurality of time-varying electrical fields induced in a left atrium 40, each crossing through the left atrium 40 in a different direction. The measurements were taken by moving a multi-electrode catheter probe 11 throughout the left atrium 40, including throughout portions of connecting lumens such as the pulmonary veins 257. It should be noted, however, that field distortions appear also in regions that were not visited, like mitral valve 36.

At each single measurement position (the field deformation at which is represented by an arrow 201), a plurality of electrodes 3 on the catheter probe 11 (all at known spacings from each other), each measured a set of voltages corresponding to the time-varying local electrical potential of the plurality of time-varying electrical fields.

It should be noted that within a given region (e.g., regions 210, 212, 214, 216, corresponding to portions of the RSPV 20, LAA 34, LIPV 22, and LSPV 23, respectively), arrows 201 tend to point in the same direction as nearby arrows, with similar magnitude. However, moving further around the periphery of shell regions central to the displacement map (e.g., around the periphery marked by shell surface 218), arrows 201 in different regions have notably different directions and/or magnitudes. In particular, the largest magnitudes shown tend to develop along several tube-like extensions of the displacement map (e.g., at regions 210, 212, 214, 216). The extensions correspond to openings in the left atrium leading to structures such as the pulmonary veins 20, 21, 22, 23, and left atrial appendage 34.

Moreover, changes in magnitude and direction generally are arranged continuously. One exception is gaps between sampled regions. The gaps are due largely to limitations on probe movement imposed by the walls of the left atrium and connected blood vessels.

Another potential exception is a small region of ambiguity 211 near the center of the figure where "streams" of arrows 201 coming from several different directions merge. This results in low distortion magnitudes (e.g., relative to whatever baseline distortion may be selected) and correspondingly uncertain (and possibly discontinuous as a result of noise in the measurement) orientations of the arrows 201. However, on shell surfaces (e.g., spherical surface 218) surrounding and slightly larger than this region of ambiguity 211, the pattern of streams becomes well-established. For example, it may be seen around the perimeter of surface 218 that nearby arrows 201 are generally oriented in directions normal or nearly-normal to surface 218.

More particularly, the overall pattern of relatively larger and smaller magnitudes (lengths) of arrows 201 already noted in peripheral regions also begins to establish within a relative short distance (e.g., within 0.5 cm, 1 cm, or another distance) from the ambiguous region 211. In particular, (1) directions of the vector arrows 201 in measurement regions 210A, 212A, 214A, and 216A match the directions of arrows from mapped regions 210, 212, 214, and 216, respectively—but with smaller magnitudes. Apart from this, (2) vector magnitudes near the center tend to remain in rough proportion to their peripheral magnitude. In FIG. 5A, this shows as central "intrusions" of slightly longer vector arrows from the directions having the strongest peripheral distortions. In some embodiments, creation of an image of a mapped region distant from its corresponding measurement region comprises amplification of field distortions determined in the measurement region and attributing them to and/or using them as indications of one or more field-affecting features in the mapped region. Optionally, the field distortions are corrected before amplification; for example: by removing components of the distortion such as the field distortion average and/or selected field distortion components.

The field distortion components may be separated, for example, by a component separation method such as FFT, PCA, wavelets, maximum likelihood or another analytical and/or statistical method. In some embodiments, the field distortion components removed represent gradual (as a function of distance) gradient changes.

Insofar as the conditions of continuity of vector direction and magnitude hold, and absent other significant short-range interference with field conditions, electrical field conditions near the surface of shell 218 may be considered as directly providing a rough map of more peripheral conditions. In some embodiments of the current invention, this feature of the displacement map is used to construct a preliminary image of the boundaries of the lumenal space. In short, impedances measured from within a relatively restricted portion of the left atrium are treated as indications of lumenal wall structure at greater distances beyond the restricted portion.

More particularly, in some embodiments, field measurements at shell positions (e.g., around the edge of a roughly spherical region of about 0.5 cm radius, 1 cm radius, or 1.5 cm radius) are directly transformed to a map (for example, such as shown in FIG. 2G), by treating angular position on the shell surface as corresponding to a more distant location, and using the amplitude of the electrical field gradient distortion as an indication of the distance of features giving rise to the distortion. For example, larger distortion is treated as indicating a more distant wall, and/or an opening in the wall.

Image Construction by Mapping from a Measurement Shell

Figure 5C:
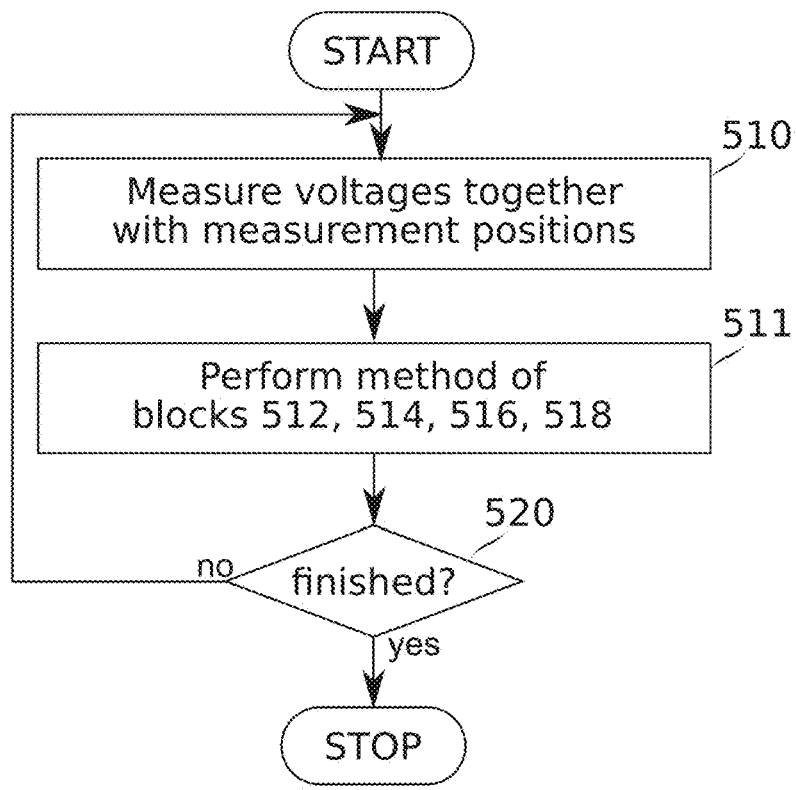

Reference is now made to FIGS. 5B-5C, which are flowcharts schematically illustrating methods for producing an image of a target body region, based on a map of anatomical structures produced using measurements from a measuring region remote from the anatomical structures of the target region, according to some embodiments of the present disclosure. FIG. 5B illustrates a method using measurements already obtained; the method of FIG. 5C includes measuring, and is optionally iterative.

At block 510 (FIG. 5C), in some embodiments, electrodes of a catheter electrode probe at an intralumenal body position are used to make measurements (e.g., voltage measurements) within an intrabody region of an electrical field. At the same time, positions of the electrode probe are measured. In some embodiments, the positions of the electrode probe are determined using the same measurements as used for producing the map, e.g., when the electrical fields measured are induced for the purpose of guiding probe positioning and/or navigation.

At block 512 (FIG. 5B), in some embodiments, the measurements are received. Voltage gradients (alternatively described as the partial derivative of voltage as a function of position) are extracted from the measurements which were recorded at positions near a periphery of the measured region. The periphery is optionally defined as regions within some selected distance from the outermost positions sampled. In some embodiments, the periphery is defined by a "rolling ball" (or pivoting ball)-type algorithm which is capable of including regions near a periphery of a measured region, while excluding measurements from a more central region. Such an algorithm may define a radius of a mathematically defined sphere which is treated as if it "rolls over" the region of the measurements, being prevented from intruding deeper into the region when it encounters a measurement position. Another parameter (e.g., a larger radius) may be used to determine the depth of the shell which comprises the region of the periphery from which measurements are extracted to determine gradients. A thicker peripheral shell potentially allows more measurements to be used; however deeper measurements may contribute to ambiguity to the gradient direction at the periphery. A larger radius rolling ball potentially reduces noise as the expense of blurring details; optionally the rolling ball size is adjusted (e.g., reduced) as more measurements become available. Optionally the size is adjusted dynamically for different regions of the periphery.

Voltage gradient may be calculated from the difference between two voltage measurements. Non-linear gradients in particular may be better represented by differences between measurements which were made at positions closer together. Conflicting gradient calculations within a same region may be resolved by any suitable method, for example, averaging, removal of outliers, and/or coherence constraints. There may also be processing to isolate position-specific gradient differences among different regions that are otherwise superimposed upon common and/or anatomical structure-irrelevant gradient changes. For example, an average field gradient may be subtracted; or a model of a field gradient that takes into account field structure in the absence of field-affecting features of interest.

There may also be one or more of at least two different types of relationships between measurements used to determine voltage gradients. In some embodiments, some measurements are made simultaneously and with known distance between each measurement (e.g., simultaneous measurements from a plurality of electrodes on a fixed-geometry electrode probe). In this case, the gradient between the two electrodes is well-determined for the period of the measurement. Additionally or alternatively, gradients are calculated between measurements made at different times. These gradients may be less precise (e.g., due to changes in the electrical field and/or lowered precision with which inter-electrode distance can be known); however, there may be many more gradient calculations of this type available.

At block 514, in some embodiments, a map of voltage gradients to angular positions is created. The map of voltage gradients, in some embodiments, may be understood as being created by projecting solid angles outward from a point somewhere within the measurement region (e.g., a center of gravity of the measurement region), and assigning the voltage gradient at the periphery region intersected by that solid angle to the associated angular position. In practice, another algorithm may be used.

At block 516, in some embodiments, a reconstruction of the target region is produced using the map, and optionally also using further constraints such as constraints on the maximum size of the mapped region obtained from other measurement modalities. In some embodiments, size constraints are provided by an echocardiogram, or an imaging modality such as MRI and/or CT.

A simple reconstruction, in some embodiments, comprises an arbitrary-sized sphere, with some representation of the map data spread across its surface. The map data may be interpreted to indicate relative depth, in which case the reconstruction sphere may be made "lumpy" to reflect relatively near and far surface regions, and/or apertures of the target region. In some embodiments, the reconstruction is sized to remain within, and/or optimally fill a space defined by some additional method. For example, a volume and/or one or more maximum dimensions may be known and used from measurements taken from an echocardiogram. Optionally, data taken during the mapping procedure itself also indicate limits of a target region. For example, indications of probe contact with a wall of the target region may be received by sensing of force and/or impedance. The position at contact is optionally used to set a constraint on positions within the reconstruction.

At block 518, in some embodiments, the reconstruction of block 516 is rendered to an image. Where the target region comprises a body lumen, the image optionally shows a surface of the body lumen in its normal 3-D form, e.g., a closed 3-D representation. Optionally, the view is from inside or outside the body lumen.

Optionally, the surface is "flattened" to create a panoramic view (viewed from any suitable angle, for example epicardially, endocardially, or any intermediate angle), for example as shown in FIGS. 2F-2G. The panoramic view, in some embodiments, is presented as a 3-D relief map of the surface. The panoramic view, in some embodiments, displays at least 80% of the total angular extent of the body lumen surface.

At block 520 (FIG. 5C), in some embodiments, the flowchart optionally returns to block 510. New measurements are used together with older measurements to produce updated gradients, map, reconstruction, and image. The cycle continues (preferably immediately; optionally after a pause) until measurement is finished.

Other Image Construction Methods

It should be understood that there is no particular limitation of embodiments of the current invention to spherical shells centered on a central region of ambiguity, where distortion vectors pointing from several different directions merge. Measurements used for reconstruction of distant features can be from any radial distance from a center, and there is no particular requirement to use only measurements from a shell-like region (e.g., the measurements can extend to include measurements at any radius sampled). The ability to recover detail may, however, be improved when measurements are taken from positions closer to the target features being reconstructed. The center itself may be chosen partially arbitrarily (e.g. whatever happens to be the geometrical center of positions of the current point set), and/or remain implicit. Biasing effects due to offsetting the center closer to/further away from features of interest are optionally corrected for, at least in part, by suitable bias subtraction and/or normalization.

It should be understood that the direct mapping process described in relation to FIGS. 3A-5A provides a particular illustration of image production, but not the only one available for use in embodiments of the present invention.

For example, iterative reconstruction techniques (e.g., algebraic reconstruction), optionally used to solve the inverse problem already mentioned, are optionally divided into five components: object model, system model, statistical model, cost function, and algorithm for minimizing the cost function.

The methods of cavity wall reconstruction described with respect to FIGS. 3A-5A may be understood as being like iterative reconstruction in their parts—but skipping the need for a cost function and iteration thereover. For example, it may be understood as using an object model in which target field-affecting features to be reconstructed are assumed to be both remote and angularly isolated (e.g., a one-layer target surrounding the measurement region). Optionally, closer and more-distant field influences are distinguished by the rate of change of the influence itself—that is, distortions which do not change quickly (e.g., are spread through more of the measurement region) are more likely due to more distant objects. Optionally, the rate of decay of distortions in the gradient ($\partial V/\partial R$) due to field influences is taken to be an exponential function of distance from the source of the distortion; for example, proportional to the inverse fifth power of distance from the source. Rate of decay of distortions in the gradient with distance, in some embodiments, provides information as to the direction and/or distance of features which cause the distortion.

The system model, in some embodiments, can be approximately summarized as: holes conduct better than walls, and electrical field gradients arrange approximately radially (after suitable correction) around centers. Use of "shells" of measurements indicates an optional, approximate statistical model wherein measuring further from the center (more in the direction of the target) is expected to give a less-noisy result. Finally, if iteration is skipped, there need be no cost function or cost minimizing algorithm selected, and the map is produced in one step as already described.

In some embodiments, any of the mentioned components of an iterative reconstruction technique is elaborated on, potentially producing more accurate results from the same input measurements.

Regarding the object model, the existence (optionally including rough sizes and/or positions) of electrically significant body features such as bones, esophagus and/or the lungs (e.g., wherein these are located beyond the cavity wall layer) can be presumed as parts of the object model which produce an influence overlaying that of nearer structures of more particular interest. It is noted that the choice, in some embodiments, to measure from within a structure, wherein the immediately surrounding parts of the structure are of particular interest, potentially simplifies choices of and/or increases available estimation accuracies of object model, system model, and/or cost function. For example, nearby structures will generally have larger and/or more localized effects on electrical field distortions. Effects of more distant structures will tend to be weaker due to distance attenuation (perhaps disappearing into the noise) and/or more diffuse (potentially allowing them to be treated as a bias that can be corrected by subtraction of an average, or another method producing a substantially equivalent bias correction). In some embodiments, a field parameter other than voltage and/or spatial voltage gradient $\partial V/\partial R$ is used in an iterative reconstruction; for example, voltage change as a function of frequency $\partial V/\partial f$ and/or field phase, $\partial V/\partial \Phi$. Optionally, the gradient is a function of a complex value such as impedance.

The system model may be developed with a more sophisticated simulation of electrical field behavior and/or tissue characteristics (electrical field simulation packages are well known and commercially available; tissue dielectric constants, e.g., for muscle, lung, blood, and bone have been published across wide ranges of electrical field frequencies).

Statistical features of measurements such as measurement noise are readily determined by previous characterization of the measurement system, and/or by repeated measurements. Noise due to movements such as heartbeat and respiration can be reduced and/or accounted for by gating to (and optionally correcting based on) independent measurements of these movements (ECG, for example), and/or cyclical indications of the movements found in the measurement data itself.

The cost function can be selected, e.g., to constrain the positions/sizes/compositions of elements of the object model to within anatomically and/or physiologically plausible limits. Any other general constraints may be added to the object model and/or cost function. For example, in structures subject to anatomical variation in different subjects, the particular anatomical variant of the current subject may be known (and used to define a cost function), or if not known, the cost function may be defined to converge on one of a plurality of likely variants.

Several choices of algorithm are available from previous work in the field of medical image reconstruction (e.g., tomographic reconstruction); for example, a range of statistical, likelihood-based iterative expectation-maximization algorithms.

Dynamic Mapping

General Dynamic Mapping

Figure 6:
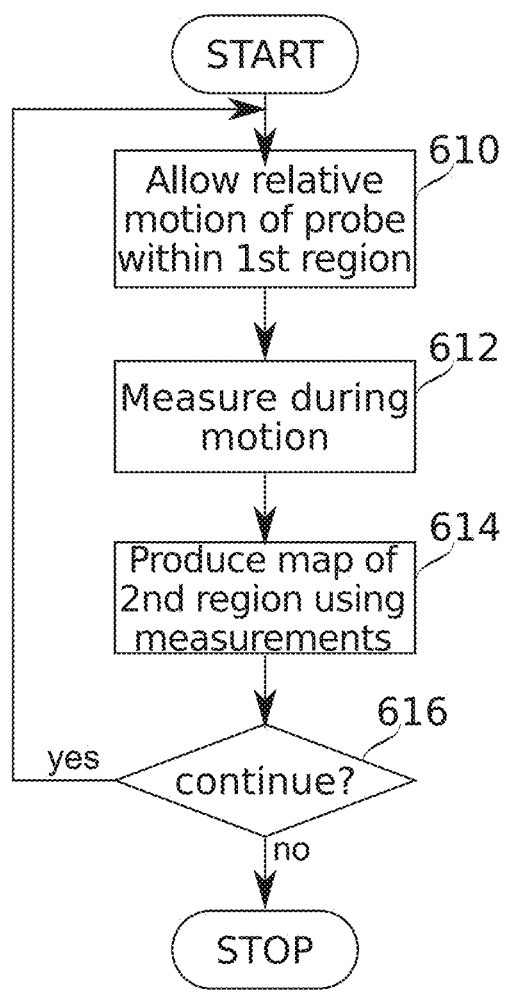
FIG. 6 is a flowchart schematically illustrating a method for updating production of a map of anatomical structures of a target body region, optionally a map displayable as an image, using measurements from a measuring region remote from the anatomical structures of the target region, according to some embodiments of the present disclosure.

Reference is now made to FIG. 6, which is a flowchart schematically illustrating a method for updating production of a map of anatomical structures of a target body region, optionally a map displayable as an image, using measurements from a measuring region remote from the anatomical structures of the target region, according to some embodiments of the present disclosure.

At block 610, in some embodiments, a measurement probe carrying measurement sensors (for example, an electrode probe 11 comprising electrodes 3) is positioned within a first body region, and begins movement within the first body region.

Optionally, the probe moves within the first body region, not according to any detailed, predetermined set of motions and/or designated targets. However, the motion may, for example, follow a generally stereotypical course; for example, crossing from a fossa ovalis of a left atrial wall to an opposite wall of the atrium. The movement overall is optionally comprised of small motions and/or reorientations of a probe, with sufficient amplitude and variety to gradually result in positioning of the measurement sensors at a variety of positions (and optionally orientations) spanning the three-dimensional extent of the first region. Optionally, portions of the movement may be described as "hovering", wherein the probe is kept generally in place, but under conditions where its position is subject to jittering (small but uncontrolled or only loosely controlled movements). In some embodiments, the jittering is e.g., within a volume of radius less than about 0.75 cm, 1.0 cm, 1.5 cm, 2.0 cm, or another radius. Optionally, portions of the movement may be described as "hunting", wherein a catheter carrying the probe is flexed to orient the probe in different directions during an otherwise generally longitudinal advance or retraction. Such motions are commonly used during advance of a catheter within a body lumen, even without the adjunct of remote impedance mapping as described herein.

The movement may be achieved by any suitable combination of small deliberate motions (e.g., advances, retractions, and/or bending control of a catheter probe), and/or uncommanded motions, for example, motions of a probe within a body lumen due to physiological movements such as heartbeat, respiration, and/or contractions of the gastrointestinal tract.

A potential advantage of such movements (e.g., a stereotyped general direction of motion with jitter and/or hunting superimposed) is that it can occur in advance of the positive establishment of the position of landmarks within the body region being navigated, relative to the position of the probe. It potentially is also relatively easy to achieve without requiring the development of a high degree of skill on the part of an operator, and may even (at least insofar as such motion is induced by autonomous movements of the surrounding body) be a natural consequence of positioning a probe in a particular place and simply waiting.

Physical exploration of the walls and/or recesses of an environment using the probe may also be avoided, while still providing (as described in relation to blocks 612, 614) an indication of where these walls and/or recesses exist. This is of potential value, since there may be some regions of the body region being mapped which are sensitive for some reason. For example, tissue walls may be prone to injury and/or edematous response upon contact. There may also be a risk of perturbing blood clots. For example, the left atrial appendage can (particularly in patients subject to atrial fibrillation) become a region of sufficiently low flow that it accumulates a blood clot. If the blood clot is disturbed during a procedure (for example, by entry of a catheter probe), then there is a risk of a portion of the clot dislodging into the bloodstream and inducing a thromboembolism elsewhere in the body.

At block 612, in some embodiments, measurements are made, during the motion. Within its context, block 612 corresponds to the intrabody measurement described in relation to block 110 of FIG. 1.

At block 614, in some embodiments, a map of a second region having features remote from the first region (e.g., features surrounding the first region, and/or features located at a distance of at least 1 cm, 1.5 cm, 2 cm, 3 cm or more from the first region) is produced. Within its context, block 614 corresponds to the production of a map of the second region described in relation to block 112 of FIG. 1. Optionally the map is further converted to a reconstruction and/or image, for example as described in relation to FIG. 5B.

At block 616, in some embodiments, a decision is made as to whether to continue the motion or not. If so, the flowchart returns to block 610, and further motion of the probe. This potentially leads to a refinement of the map at block 614, for example as now described in relation to FIGS. 7A-7B. Otherwise, the flowchart ends (optionally to enter into a new phase of mapping and optionally image production).

Image Refinement with Increased Measuring

Figure 7A:
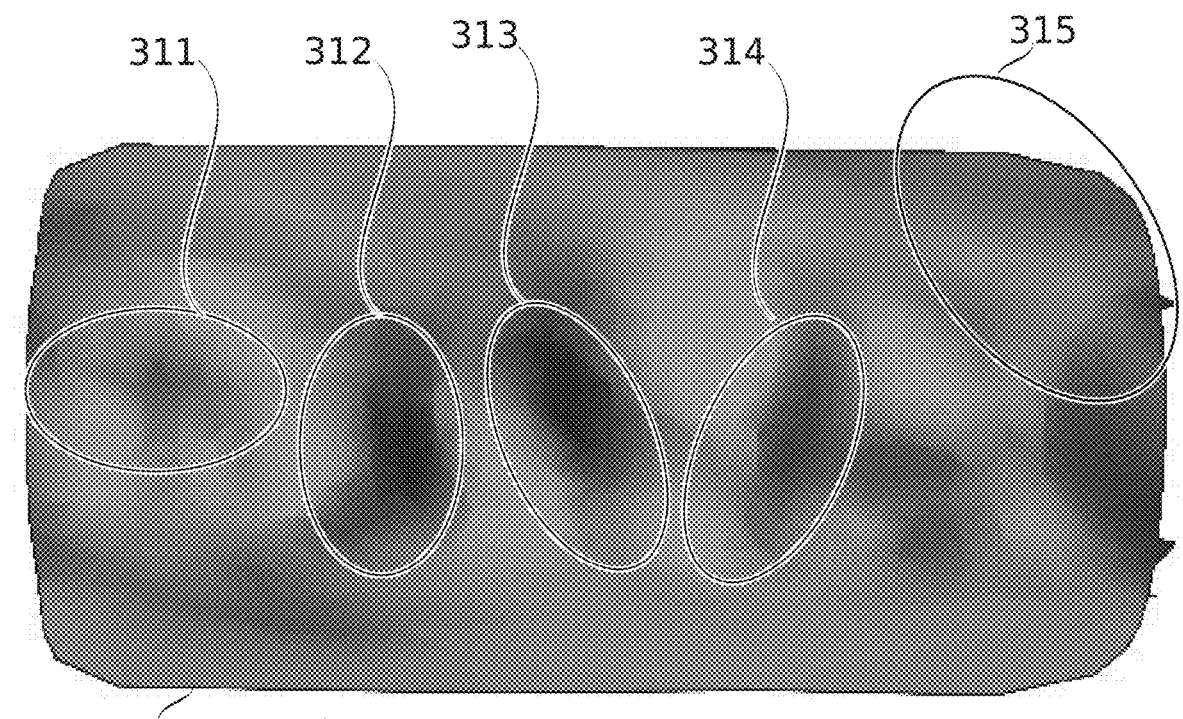
FIGS. 7A-7B show images produced from an early-phase map and a later-phase map of a body lumen wall structure (each displayed as "endocardial" images) based on a cumulative set of intralumenal voltage measurements at positions remote from anatomical structures of the target region, according to some embodiments of the present disclosure.
Figure 7B:
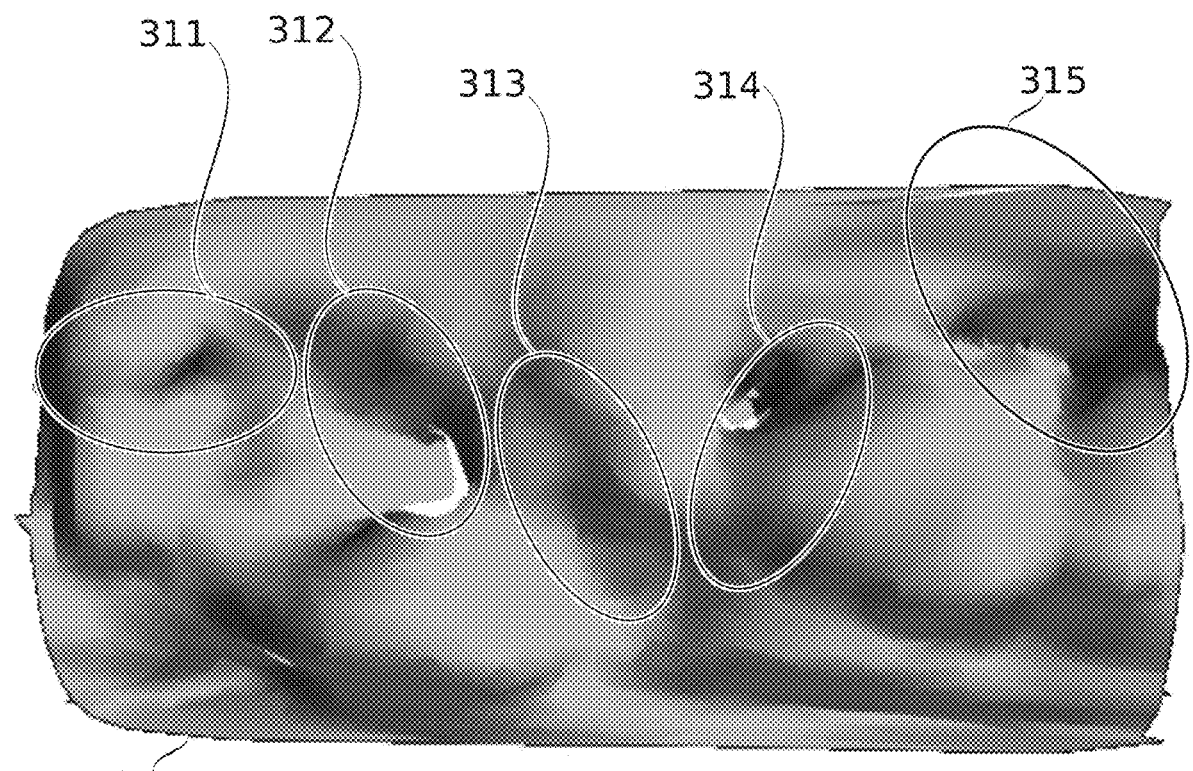

Reference is now made to FIGS. 7A-7B, which illustrate an early-phase image 302, based on an early-phase map; and a later-phase image 303, based on a later-phase map. The early- and later-phase images 302, 303 are of a body lumen wall structure, and based on a cumulative set of intralumenal measurements (e.g., voltage and/or impedance measurements) at positions remote from the body lumen wall, according to some embodiments of the present disclosure. The images themselves are also maps, transformed from the 3-D representation used in the source maps on which they are based.

The body lumenal wall structure of FIG. 7A-7B images positions of walls and recesses (e.g., lumens) of the interior of a left atrium. The view shown is a panoramic view; constructed for example, as described in relation to FIGS. 2A-2G.

Indicated in both early-phase image 302 and later-phase image 303 are mutually corresponding features 311, 312, 313, 314 and 315. Feature 315 corresponds to a left atrial appendage. The other indicated features each correspond to the positions of the several pulmonary veins.

It may be seen, by comparing corresponding features in FIGS. 7A-7B that there is a general progression, as more data is obtained (still within a restricted first region), toward a more detailed map of the features shown. There is potentially some migration of the imaged position of features as detail is added; for example, pulmonary vein 312 acquires an offset over time to reach a slightly different position in FIG. 7B compared to FIG. 7A. This may be, for example, a function of how resolution is increased, and/or how a reconstruction of an anatomical structure made using the map is oriented in the image (this is described, for example, in relation to FIGS. 9A-9B). Within maps on which the images are based, angular positions are generally found to be stable once a feature is recognized.

Even the less-detailed map still provides an indication of the general positions of features which can be used to guide new navigation. Moreover, as will now be described, another feature of the mapping method, in some embodiments, is that it is amenable to refinement not only as a function of increased numbers of measurements overall, but also as a function of the proximity of measurements to the mapped region.

Image Refinement Using Increased Measuring Directed from Image Appearance

Figure 8:
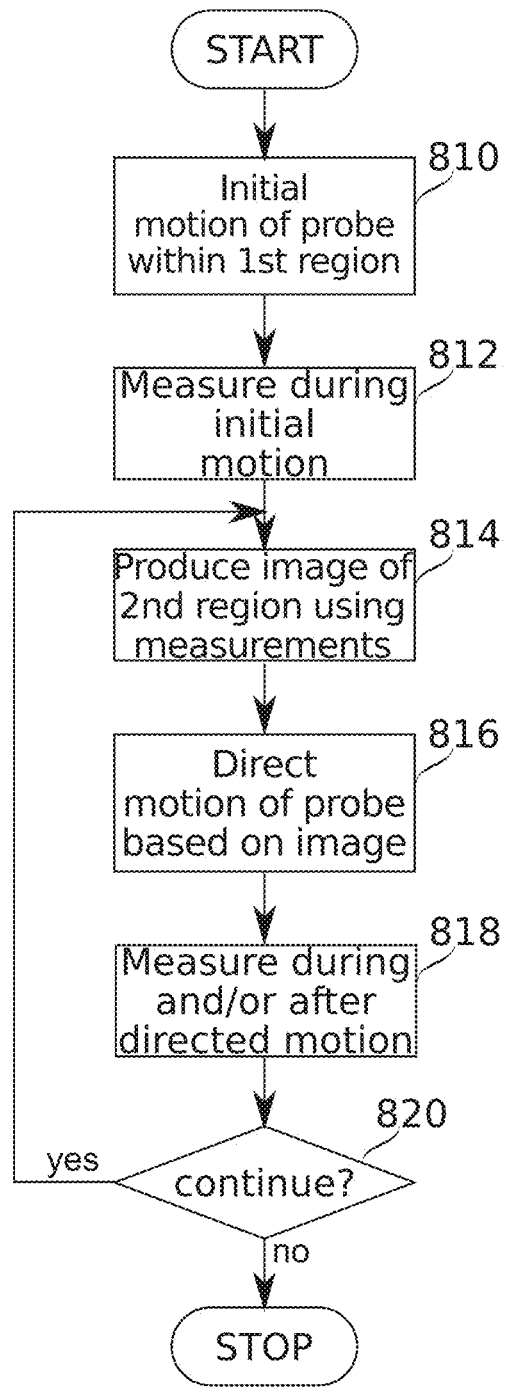
FIG. 8 is a flowchart schematically illustrating a method for production and refinement of a map of anatomical structure of a target body region, using display of the map as an image, and using measurements from a measuring region remote from the anatomical structures of the target region, according to some embodiments of the present disclosure.

Reference is now made to FIG. 8, which is a flowchart schematically illustrating a method for production and refinement of a map of anatomical structure of a target body region, using display of the map as an image, and using measurements from a measuring region remote from the anatomical structures of the target region, according to some embodiments of the present disclosure.

The flowchart begins at block 810, with initial movement of a measurement probe within a first body region. Block 810, in some embodiments, corresponds to the operations of block 610 of FIG. 6. Optionally, the initial motion of a measurement probe in block 810 is directed within a limited region; comprising, for example, a lumen crossing with jitter and/or hunting, and/or a deliberate sweeping of a catheter probe in a pattern that densely samples a selected first body region. The measurement during initial motion of block 812, and production of a map, and an image therefrom in block 814 correspond to the operations of blocks 110 and 112 of FIG. 1.

It is noted that (for example, because the position of the measurement probe is known in association with the measurements of block 812), the map which is produced at block 814 is easily placed in registration with the current measurement probe position. This allows production of an image from the map (e.g., via a reconstruction of the target body region) that shows both target region and probe in their relative positions. In some embodiments, the probe position is displayed along with the image produced at block 814 (this feature may also be provided along with operations performed in association with the methods of FIGS. 1, 6, and 10, for example).

At block 816, in some embodiments, directed motion of the probe is performed, based on the image produced at block 814. Optionally, this comprises manipulating the probe based on its indication on the image produced at block 814 to approach and/or orient toward one of the features (or featureless regions) shown on the image.

At block 818, in some embodiments, measurement is performed during the directed motion (for example, as described in relation to block 110 of FIG. 1). At block 820, in some embodiments, a decision is made as to whether or not to continue.

If so, the flowchart returns to block 814, and the production of a new map and image. Insofar as it incorporates new measurements (preferably while retaining measurements of block 812 and/or previous measurements of block 818), and in particular new measurements related to the motion and/or orientation toward the target of block 816, the new image is potentially more detailed in one or more regions of interest.

Otherwise, the flowchart ends (optionally to begin a new phase of navigation and/or mapping; optionally to perform a treatment at the region navigated to).

Figure 9A:
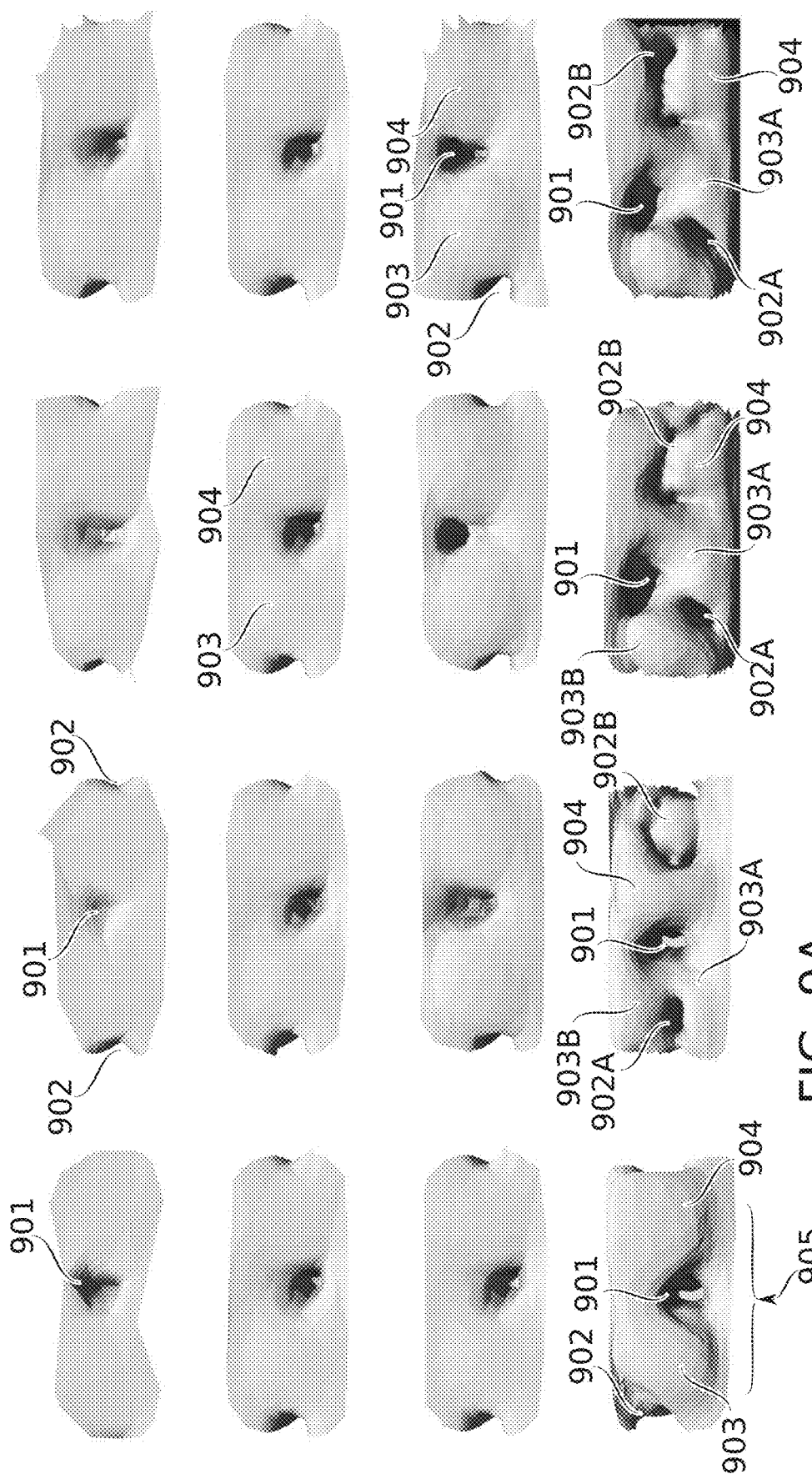
FIGS. 9A-9B each show a sequence of images produced from earlier-measurement phase maps, and later-measurement phase, more refined maps of body lumen wall structure, based on a cumulative set of intralumenal voltage measurements at positions remote from the body lumen wall, according to some embodiments of the present disclosure.
Figure 9B:
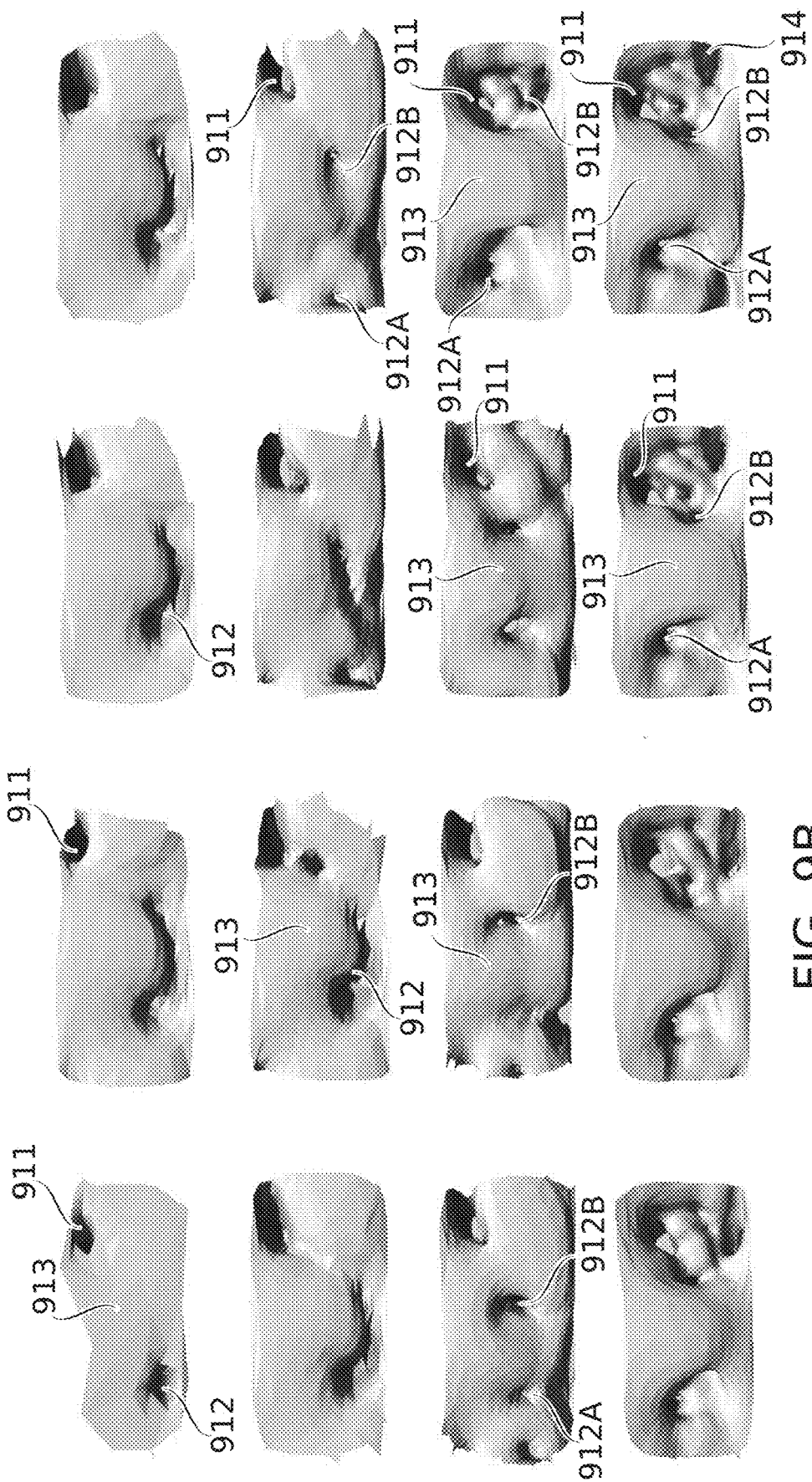

Reference is now made to FIGS. 9A-9B, which each show a sequence of images produced from earlier-measurement phase maps, and later-measurement phase, more refined maps of body lumen wall structure, based on a cumulative set of intralumenal voltage measurements at positions remote from the body lumen wall, according to some embodiments of the present disclosure. Measurements used are from a patient. Each of the two image sequences will be described with reference to certain selected features shown, and their evolution throughout the sequence. The sequences each proceed in time from left to right and from top to bottom (i.e., the upper-left image is the first image in the sequence, the image below it is the fifth image in the sequence, and the image in the lower right is the sixteenth and last image in the sequence). Images are displayed as endocardial panorama views, for example as described in relation to FIG. 2G, herein. The imaged regions shown as the mapped second region comprise interior surfaces and connecting lumens, apertures, and/or cavities of a left atrium.

In FIG. 9A, the initial image produced (e.g., from a map via a reconstruction using the method of FIG. 5B) was obtained by an electrode probe just after passage of the fossa ovalis from the right atrium into the left atrium. It is very low in overall detail resolution, and shows essentially just one putative lumen 901 (which has been automatically assigned to the central position in the unwrapped panoramic image, based on a weighting algorithm that seeks to put the "center of mass" of features distributed over the surface of the map at the center of a panoramic image produced from the map).

The catheter tip was advanced across the left atrium, crossing the space in a "hunting" mode, with the tip often being flexed to displace and orient the electrode probe itself in different directions. The displacement served to expand the width of the region being sampled during catheter tip advance.

The flexing changes in probe orientation also had effects on the quality of measurement data for determining local gradients, potentially for reasons now explained. In this example (and also in the example of FIG. 9B), the electrode probe used was a multi-electrode probe, wherein the electrodes were spaced from one another at well-known and fixed (relative to each other) positions. In this configuration, electrical field gradients were measured with lowest error from simultaneous readings from the different electrodes, since their relative distances were known with high precision. Gradients measured between measurements obtained at different times, on the other hand, were subject to more error, due, e.g., to uncertainties in position determination and/or dynamics of the field itself (e.g., due to heart and respiration movements). When the probe was oriented substantially perpendicular to the field gradient, very little gradient could be sensed using the low-error mode, so details revealed themselves only slowly as enough signal could be acquired to overcome the noise source. However, when the probe was oriented more nearly pointed into (or away from) the gradient, low-error gradient sensing became possible, allowing features positioned in the direction of the gradient to be detected.

Accordingly, as measurement continues (preferably immediately; optionally after a pause), an apparent second aperture 902 appears in the images, offset from the first by about 180° (feature 902 appears split, because it straddles the division made to splay the atrium surface into a panoramic view). Later in the crossing (in the second row of four images), two relatively raised regions 903, 904 also make an appearance. The raised regions, however, are potentially better characterized as (currently) "feature free" regions, relative to the relative receded regions corresponding to directions which have been better measured so as to reveal features of the gradient. All of these features move around slightly as the addition of new measurements results in a change in the center of mass of the features represented by the images of FIG. 9A. By the end of the third row, the recessed features identified are represented with relatively high resolution (sharper edges generally, for example, and resolution of two holes within region 901). However the detail available remains limited by the restricted initial sampling region and probe orientations used.

Beginning in the fourth row, the initial crossing has been completed, after a few seconds (e.g., about 5-10 seconds). The probe is now retracted toward the middle of the left atrium, and deliberate catheter flexures initiated to more thoroughly gather measurements from incompletely sampled direction. As a result, aperture feature 902 now splits into two sub-features 902A, 902B. Region 903 splits into two subregions 903A, 903B. After revealing some new detail in area 902B, the probe orients toward the region of features 901 and 902A, making measurements that finally appear to resolve them as the left PVs and the right PVs, respectively. These veins are optionally treatment targets, e.g., targets of a line ablation procedure intended to electrically isolate the pulmonary veins so that they can no longer transmit impulses to the atrium which can result in uncoordinated contractions and/or atrial fibrillation. In the final image of the sequence, the probe has returned to visit the region of feature 902B, which now resolves as the apparent aperture leading to the mitral valve (at far right of the darkened region indicated as feature 902B), and another region (the left lobe of the darkened region 902B) which apparently indicates the LAA. Optionally, a user is presented with an interface allowing manual tagging of features as their identities become apparent. Optionally, features are identified automatically based on their characteristics, individually and/or in comparison with other resolved features.

It should be noted that at this stage, the level of relief of blood vessels typically is less than 1 cm or so. For greater depth and the resolution of other details, the measurement probe can be advanced to individually visit features shown on the left atrial wall, for example as described in relation to FIGS. 11A-11D.

Turning to FIG. 9B, two aperture-like features 911, 912, and one raised area 913 (really a "featureless" region) are initially visible upon entry of the electrode probe into the left atrium via the fossa ovalis (again, orientation of the panoramic view is set by a center-of-gravity algorithm). Crossing-mode (advance with tip flexures) collection of measurements results in refinement of this picture up to about the second image of the second row. The direction of feature 912 (near the lower middle of the image) is selected as a first target for refinement, and the probe is oriented in that direction. This allows feature 912 to become resolved into two distinct apertures 912A, 912B, with raised area 913 acquiring some feature texture and protruding in-between. By the last image of the third row, the probe has been oriented to explore the gradient in the direction of feature 911, which is revealed as partially merging with feature 912B. The final image (at lower right) reveals the right pulmonary veins within region 912A (the two lobes of the darkening there apparently corresponding to the ostia of the superior and inferior right pulmonary veins). The ostia of the left pulmonary veins are joined adjacent to one another (comprising feature 912B) in a depression in common with the left atrial appendage (corresponding to feature 911), with a recessed ridge in between. Raised region 913 remains featureless extent extending between the left and right pulmonary vein ostia. Another depression 914 has also become apparent, apparently associated with features of the mitral valve.

It should be understood that the method of mapping refinement discussed in relation to FIGS. 9A-9B can also be integrated with other sources of mapping information. In some embodiments data from contact mapping (wherein the exact position of a wall is known by some feature of force, impedance, or another property which changes upon contact of a sensor with a lumenal wall) is substituted for remote-mapping data at positions where it is available, and/or used to help set relative scales of features applied to a reconstruction which is used as a basis for producing a panoramic image, or a closed-surface epicardial image. Examples of mapping enhanced by additional exploration are shown in FIGS. 11A-11D. For example, the double apertures visible within the ostia of the RSPV and RIPV in FIG. 11D are a result of exploration by the measurement probe substantially within the ostia themselves. Also, the longitudinally extended PVs prominent particularly in FIGS. 11A and 11C extend for more than 1 cm, which is potentially an approximate limit of the map using only remote measurement data.

A notable remotely-imaged feature of FIG. 11B is indicated as esophageal bumps 37. Such bumps, though displayed, are not necessarily found on the actual surface indicated in the image—rather, they are a result of a significant field-affecting feature located behind the surface: the esophagus. In some embodiments, a mismatch between the position of the surface as measured by contact measurement and a position of same surface as indicated in the image is used to identify that there is a particular anatomical feature (such as an esophagus) behind the surface.

The esophagus position is a concern for avoiding complications from ablation procedures, as burns or other damage to the esophagus made during an ablation procedure can result in a situation serious to the point of causing death.

The esophagus comprises a lumen having some air in it, so the relative conductive properties are the reverse of those of blood (less conductive). This leads to the appearance of lowered gradient/more widely separated field lines for portions of the electric field gradient which point in its direction. The possibility to detect the esophagus directly from an intralumenal probe (in some embodiments, the same probe as is used to ablate) is a potential advantage for simplification of the procedure, and/or providing a potentially more accurate capability to avoid inadvertent esophageal ablation. For mapping within a right atrium (not shown), another important piece of anatomy existing beyond the lumenal surface itself is the aorta, which also should not be damaged by treatments, and which may be visible in an image of a remote impedance map as a partial cylindrical indentation apparent on the (actually smooth) right atrial wall. In some embodiments, the anatomical source of such non-surface caused surface distortions is verified by moving a probe close enough to the distorted surface, and observing that the probe, when positioned in contact with the wall, is in a position different than the one indicated by the non-surface caused distortion.

Figure 13:
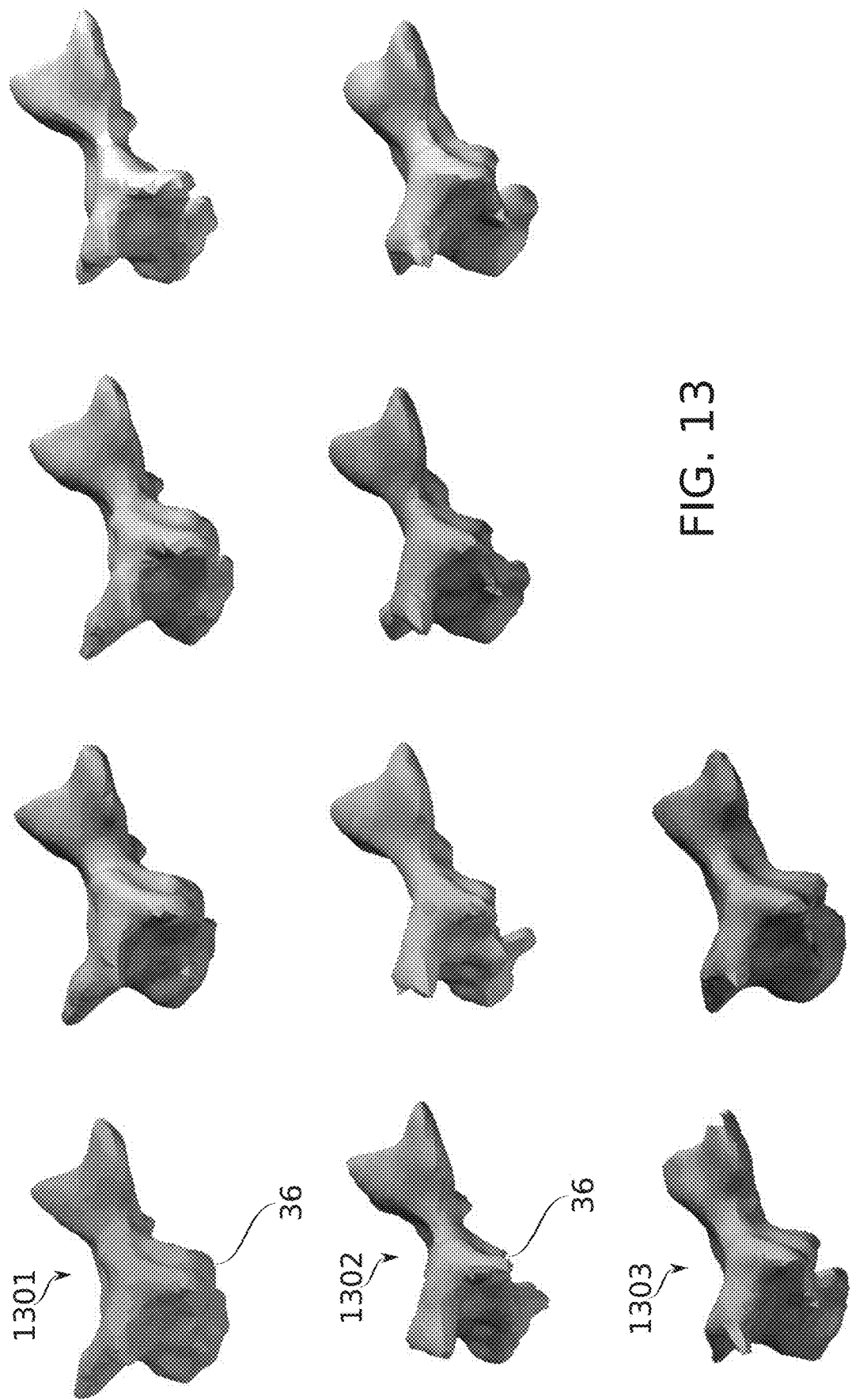
FIG. 13 shows selected frames of a cine of a beating left atrium, generated based on remote field sensing maps, according to some embodiments of the present disclosure.

Optionally, production of a map uses gating (e.g., by heartbeat and/or respiration data) as an input to select and/or correct measurement data used to produce the map. An example of the use of heartbeat phase gating to produce a cine sequence of frames showing motion over the course of a heartbeat cycle is shown in FIG. 13.

Image Refinement Using Increased Measuring Directed to Image Targets

Figure 10:
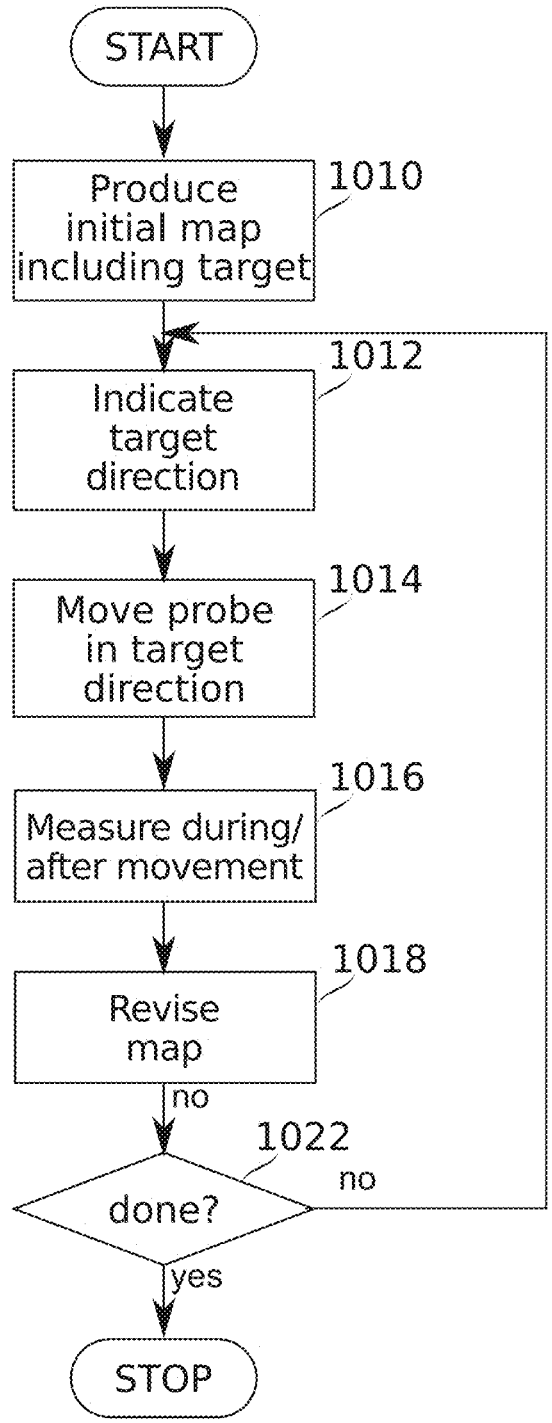
FIG. 10 is a flowchart schematically illustrating a method for guidance to a region of a body using a map of the region produced from remote measurements from an electrode, according to some embodiments of the present disclosure.

Reference is now made to FIG. 10, which is a flowchart schematically illustrating a method for guidance to a region of a body (e.g., lumen wall) using intralumenal measurements, according to some embodiments of the present disclosure.

In some embodiments, image data (optionally including image data constructed, e.g., from a reconstruction of a body region) from a different imaging modality are available which can be registered to a probe's current frame of reference using the positions of reference structures identified using remote impedance mapping (and/or remote mapping of another field type, e.g., according to a method described in relation to FIG. 1). More generally, the relative arrangement of features of the remote field map are optionally used to help determine registration parameters for any instance where a probe position (well-known relative to the map, since it is being used to generate the map) is to be placed relative to some other data representation (in distance, and/or based on its relative angular position) which also includes representations of the same features.

A remote impedance-sensing map can also be used in non-imaging applications to generate instructions for motion of a catheter probe to reach a certain target region. The instructions can be in the form of instructions to a user (for example, indicators on a display), and/or instructions applicable to use by an automatic (robotic) navigation system.

At block 1010, in some embodiments, an initial map is produced including an indication of a target for navigation (for example a feature represented in the map like one of features 901, 902A, 902B of FIG. 9A, or any sub-region thereof). The map is produced using measurements from an intrabody probe which is to be navigated to a target, for example, according to the method of FIG. 1.

At block 1012, in some embodiments, an indication is provided of a direction for catheter motion. Optionally, the indication is shown as a direction, relative to a map-registered image generated from a non-remote impedance imaging source such as an MRI, CT, and/or ultrasound image. Alternatively or additionally, the indication is provided as instructions of how the manipulate the catheter itself. Generation of the instructions optionally takes into account the particular mechanical behaviors of the catheter being used. The instructions may be provided to a human operator, and/or a robotic operator.

At block 1014, in some embodiments, the probe is moved in the direction of the initial target, based on the indication of block 1012.

At block 1016, in some embodiments, measurements are taken during and/or after movement of the probe (for example as described in relation to block 110 of FIG. 1). This may result in enhanced resolution of the target region; for example, insofar as the probe is likely to now be oriented toward the target and so measuring with electrodes spaced along an axis running nearly parallel to the gradient.

At block 1018, in some embodiments, a new map is produced using at least the new measurements. Also at block 1018, in some embodiments, the new map is optionally evaluated for evolution of target within the map (compared to the previous map). For example, an initial single target lumen may resolve into two target lumens. Optionally, the current target is updated accordingly, e.g., automatically to select a superior or inferior PV as indicated by a current treatment plan, or by a choice of a user.

The flowchart moves to block 1022. If the movement is complete, the flowchart ends. Otherwise, the flowchart returns to block 1012, with an updated indication of target direction.

Other Lumenal and Non-Lumenal Sensor and/or Target Configurations

Examples provided herein generally relate, for purposes of description, to mapping from a first region of a remote second region which comprises a body cavity (e.g., a heart chamber, lumen of the gastrointestinal system, brain ventricle, or other body part comprising a hollow region). The first region itself is generally shown in the examples to be positioned within the hollow of the second region.

However, it may be readily understood that the first region may, in some embodiments, be part of an intrabody hollow nearby (including outside of), rather than within, the second region which is targeted for mapping. For example, the first region may be an intraperitoneal space, and the second region may be an abdominal organ such as a liver, kidney, uterus, or other organ. The second region need not itself comprise a hollow in this configuration.

Furthermore, there is no requirement, in some embodiments, for the first region to be within a hollow either. For example, an electrode may be placed upon a needle which enters a region of solid tissue (fat, lung, muscle, and potentially even bone). The probe sensor movement which allows sampling of a local region of field measurements (e.g., electrical and/or magnetic field measurements) can be accomplished by natural movements of and/or relative to the solid tissue, palpitation of the tissue with the sensor embedded, and/or movement of the sensor within whatever limited range of positions is allowed by its insertion track.

The sensing probe need not even necessarily be positioned at an intrabody position. For example, electrical and/or magnetic field-based tracking methods can be configured to work using a probe which is positioned outside a living body. The probe can be moved within such a body-external region, allowing it to make measurements at several known positions within that region. The set of measurements can then be analyzed as described for the intralumenal configuration (albeit, just for the side occupied by the body of interest). It is noted that such a configuration can be distinguished from spacing sensors surrounding a target region, or even moving sensors in circumferential paths around a target body region within a surround, insofar as the region within which the sensor moves to sample a field is located to one side of the region which is being imaged. While this potentially reduces the ability to reconstruct, for example a complete tomographic section of a body, there is a potential advantage for mapping of structures which are arranged relative near to a body surface.

Other Field Types

Examples provided herein generally relate, for purposes of description, to mapping based on electrical sensing by one or more electrodes on a probe. However, it should be understood that the same principles apply, changed as necessary, to measurements of other fields. Magnetic fields provide an example which is similar in several respects to the electrical field, e.g., it can be described in terms of sources and sinks (poles rather than charges), follows an inverse square law, and is subject to some (though potentially not as much in the case of biological tissue) distortion as a function of the media it passes through.

Other Structural Features and Related Measurement/Analysis Approaches

Examples provide herein generally relate, for purposes of description, to mapping which uses field properties to infer the topographical structure (geometry) of the target body region being mapped (e.g., lumenal wall shape). However, it should be understood that there is no particular limitation to this. Topographic structure in particular may be derived from electrical field data (for example), because there is a sufficiently large dielectric property difference between fluids filling a cavity (blood, water, and/or air, for example) and the tissue wall of the cavity itself. However, there can also be differences in dielectric properties (taken as one example of a material property which affects characteristics of a particular field type) which do not appear as topographical boundaries. For example, in heart tissue, impedance differences may be observed between scarred and healthy myocardial tissue. In some embodiments, processing of field measurements within the remote region includes processing to reveal such microstructural differences among different tissue regions.

In some embodiments, revealing these differences comprises performing measurements at a plurality of different electrical field frequencies, which potentially helps to distinguish frequency-dependent dielectric property differences among different tissue types. The processing performed optionally includes a differential step, for example comparing the distortion difference at two different frequencies, as a way to amplify field distortion features that are attributable to the particular material composition of an anatomical structure.

Quality Indication

It is noted that remote images made based on field measurements within a more local region potentially include at least some implicit indication of map quality, insofar as they proceed from a less detailed/less resolved representation of details to a more detailed/better resolved representation of details. An operator can also observe if/how an image changes over time to form an implicit judgement about the current quality of the map the image is derived from.

In some embodiments of the invention, an explicit indication of current estimated map quality is provided in addition to what can be determined by inspection of the image itself as produced from the map. In some embodiments, quality is automatically estimated on one or more suitable metrics; for example: based on number of samples used in the map (overall and/or in particular areas), converging variability of map and/or map region results (e.g., as the map is updated, how much it has changed over some recent period of time), estimated noise within the field measurement samples used to produce the map (e.g., estimated signal-to-noise ratio within measurements taken from nearby positions), and/or another metric of map quality.

In some embodiments, map quality is represented to an operator by the presentation of at least one scale bar representing the quality metric or metrics which are implemented. The scale bar is optionally presented together with an image of the map (e.g. as an overlay), or as an indication on a separate display. Optionally, map quality is represented by another visual indication, for example, a number, icon and/or color sequence, and/or threshold indicator (crossing/not having yet cross a certain quality threshold) such as an icon and/or color. In some embodiments, map quality is signaled by one or more auditory tones.

In some embodiments, indications of map quality are presented on the map-representing image itself, for example, by changing a hue, saturation and/or intensity of the image representation. In some embodiments, the image quality is represented as a difference in quality from a previous image. For example, regions where quality is updated recently are shown with a difference in a hue, saturation and/or intensity of the image representation.

Figure 12:
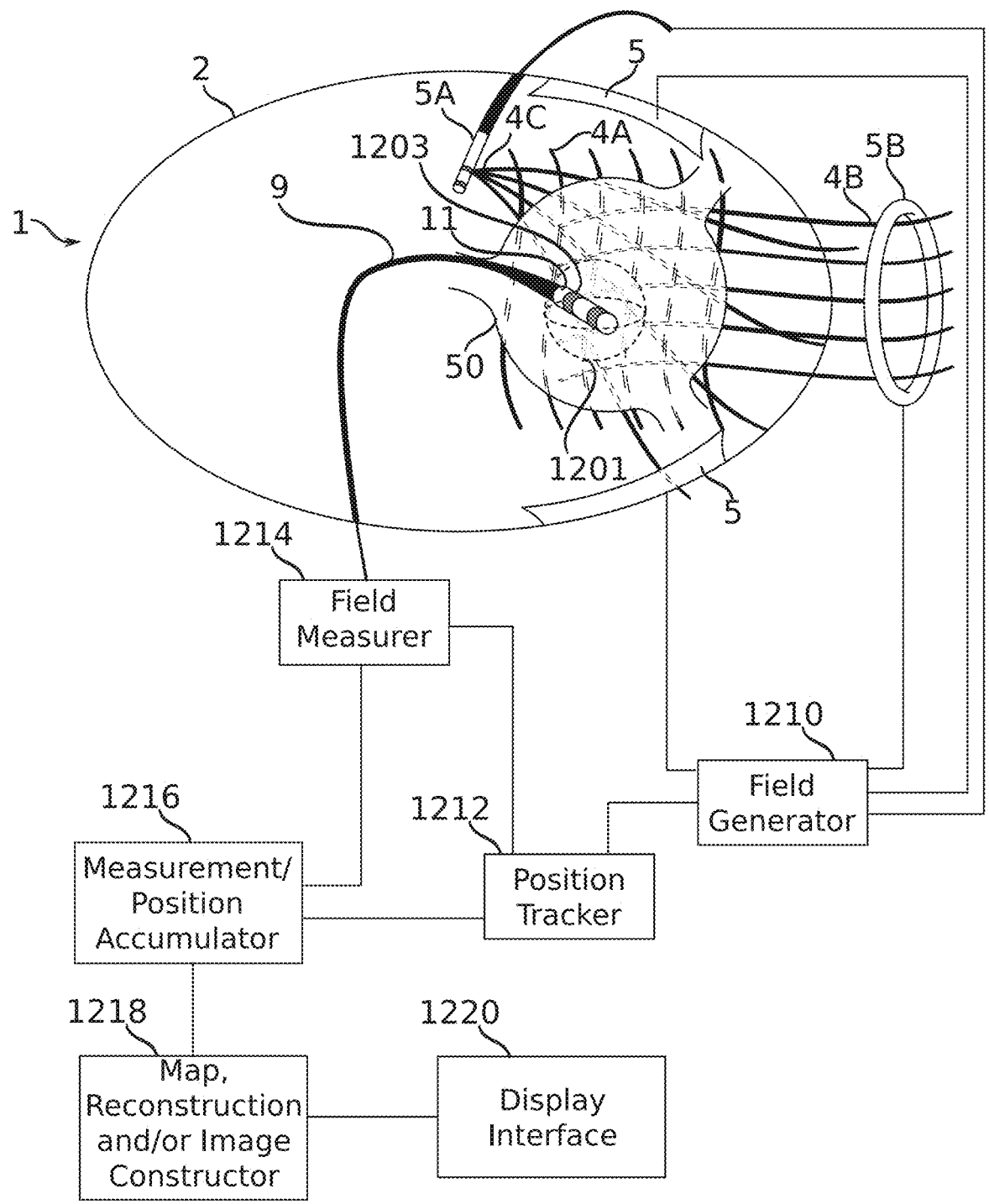
FIG. 12 schematically represents a system for remote mapping of body regions based on field sensing, according to some embodiments of the present disclosure.

Systems for Remote Imaging Based on Position-Referenced Sets of Field Measurements Reference is now made to FIG. 12, which schematically represents a system 1 for remote mapping of body regions based on field sensing, according to some embodiments of the present disclosure.

Several illustrative examples are shown of system components capable of inducing measurable fields 4A, 4B, 4C which extend through a target region 50 of a living body 2 (e.g., a left atrium of a heart of a patient). In the case of an electric field, for example, the measurable field may be measurable, e.g., as an electric signal produced at positions within its extent, on one or more probe electrodes, and measured as a voltage, impedance, current, phase, frequency or other characteristic attributable to an influence of the field on the probe electrode.

One or more pairs of body surface electrodes 5 are optionally used to induce one or more time-varying (e.g., radio frequency) electrical fields 4A. One or more inducing electrodes of catheter probe 5A are optionally used to generate one or more time-varying electrical field 4C. Optionally, one or more inducing electrodes of catheter probe 5A, positioned outside target region 50 are used to generate one or more time-varying electrical field. Electromagnetic coil 5B is optionally used to generate one or more magnetic fields 4B. The fields (of whatever type) are generated using one or more field generators 1210. Optionally, fields generated by field generator 1210 are also used in position tracking, and field generator 1210 is configured in communication with position tracker 1212 for this purpose.

Probe 11 (optionally an electrode catheter probe) is used together with a positioning means 9 (e.g., catheter) to control positioning of field sensor(s) 1203 (which in some embodiments comprises one or more electrodes 3). While sensor(s) 1203 are positioned within measurement region 1201, they sense local conditions of one or more fields, e.g., fields 4A, 4B, and/or 4C. Sensed conditions may be converted to numeric measurements by field measurer 1214, and the measurements may be transferred to measurement/position accumulator 1216. Optionally, the field measurer 1214 is in functional communication with position tracker 1212 (e.g., in embodiments wherein the local field environment of probe 11 is used for position tracking by position tracker 1212).

The operations of these components (in whatever configuration used), up to the collection of data by measurement/position accumulator 1216 correspond, in some embodiments, to block 110 of FIG. 1.

Measurement/position accumulator 1216 may be configured to pass measurements to map, reconstruction, and/or image constructor 1218. Constructor 1218 may comprise a processor, a memory, and processing instructions which, when executed, cause the processor to produce a map of target region 50, for example as described in relation to block 112 of FIG. 1. Optionally, the constructor is also configured to produce a 3-D reconstruction of the target region 50, and/or an image of target region 50 generated directly from the map, and/or from the 3-D reconstruction Measurement/position accumulator 1216 and constructor 1218 optionally are used in other methods described herein (e.g., in relation to FIGS. 6, 8, and/or 10) to continue accumulating measurements and producing new images during the course of a procedure. In some embodiments, constructor 1218 is provided as a modular device (e.g., comprising processing instructions, a processor, and/or a memory) which is configured to receive electrical field measurements and/or position tracking information (e.g., from a separately provided electrical field measurer 1214 and/or position tracker 1212), and produce an image therefrom.

Display interface 1220 may comprise a display used to show images produced by constructor 1218. Optionally, display interface 1220 is part of a general user interface (additionally comprising an input device such as a mouse, keyboard, and/or other input device) configured to allow interacting with the produced images (e.g., to change viewing parameters such as scales and view angles).

Imaging of Heartbeat-Phase Imaging Based on Position-Referenced Sets of Field Measurements Reference is now made to FIG. 13, which shows selected frames of a cine of a beating left atrium, generated based on remote field sensing maps, according to some embodiments of the present disclosure.

Each of rows 1301, 1302, 1303 shows a set of four individual frames of a cine image of a beating left atrium. The ten images shown are themselves extracted from an original set of 75 images, representing one heartbeat cycle. The represented heartbeat cycle was generated by merging data from about 10 heartbeat cycles, with measurement segmented to different frames according to the phase of the heartbeat cycle wherein it was taken. Of particular note is a structure corresponding to mitral valve 36. At the beginning of row 1301, valve 36 is open (downward), visible as a bulge below the line of an adjacent pulmonary vein. By the beginning of row 1302, valve 36 is closed again. The motion of the valve can be followed throughout the cycle (which returns to row 1301 after completing row 1303).

As a whole, the frames of FIG. 13 represent an option for producing heartbeat phase-resolved images, potentially allowing catheter probe-measured images of functional and/or disease states to be generated during a catheter procedure. One potential use of this is to check whether or not a patient has had a partial paralysis of a heart portion during a procedure, which can potentially lead to complications warranting extra medical attention during procedure recovery.

General

As used herein with reference to quantity or value, the term "about" means "within ±10% of".

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example" or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Throughout this application, embodiments of this disclosure may be presented with reference to a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features, which are, for clarity, described in the context of separate embodiments within the present disclosure, may also be provided in combination in a single embodiment. Conversely, various features, which are, for brevity, described in the context of a single embodiment, may also be provided separately or in any suitable subcombination or as suitable in any other described embodiment of the present disclosure. Certain features described in the context of various embodiments are not to be considered essential features of those embodiments, unless the embodiment is inoperative without those elements.

What is claimed is:

1. A method of producing an image using measurements of at least one electrical field made within a first region of a body, the method comprising:
   for each of the at least one electrical fields:
   receiving a plurality of measurements of voltages of the electrical field measured using an intrabody probe at different positions within the first region, and
   mapping voltage gradients of the electrical field to the first region, using the voltage measurements;
   analyzing the mapped voltage gradients to identify distortions in the at least one electrical field;
   determining positions of apertures in a tissue wall located outside of the first region using the identified distortions as indications of the presence of the apertures at said positions; and
   producing an image showing the tissue wall and the apertures.

2. The method of claim 1, wherein the received measurements were obtained using a plurality of electrodes positioned at known distances along the intrabody probe, and the voltage gradients indicated by the voltage measurements are determined based on the voltage measurements and the known distances.

3. The method of claim 1, wherein the voltage gradients comprise a plurality of different local voltage gradients within the first region.

4. The method of claim 1, wherein the producing an image uses voltage gradients from near a periphery of the first region, the near periphery being defined to exclude voltage gradients from a central portion of the first region.

5. The method of claim 4, wherein the determining positions of the apertures comprises setting distances from the first region to portions of the tissue wall surrounding the apertures as a function of gradient strength near the periphery of the first region.

6. The method of claim 5, wherein the producing the image comprises setting distances from the first region to features of the image based on a map of voltage gradient strength near the periphery as a function of solid angle.

7. The method of claim 4, wherein the producing the image comprises setting distances from the first region to features of the image as a function of a decay of a distortion in voltage gradients with distance.

8. The method of claim 1, comprising producing a plurality of images corresponding to a corresponding plurality of different heartbeat phases, based on a heartbeat phase during which the voltage measurements were measured.

9. The method of claim 1, comprising: receiving contact measurements, measured while the probe contacts the tissue wall; and identifying a feature of the image which indicates an anatomical structure located behind the tissue wall, based on a mismatch between the position of the surface as measured by the contact measurements and a position of same surface as indicated in the image.

10. The method of claim 1, wherein the image is produced within about 5 seconds of receiving the first measurements.

11. The method of claim 1, wherein said producing an image showing the tissue wall and the apertures comprises producing a plurality of portions of an image of the tissue wall, each corresponding to a respective portion of the first region, wherein each portion of the plurality of portions of the image of the tissue wall has in common with the respective portion of the first region an angular position with respect to a reference location.

12. The method of claim 11, wherein each of the plurality of portions of the first region is between the reference location and the respective imaged portion of the tissue wall.

13. The method of claim 1, wherein a plurality of respective portions of the first region and of the image are in correspondence, such that the image portions are each respectively indicated by measurements from the respective corresponding portion of the first region.

14. The method of claim 1, wherein the tissue wall comprises a lumenal wall of a body cavity.

15. The method of claim 14, wherein the lumenal wall is a wall of a cardiovascular lumen.

16. The method of claim 15, wherein the cardiovascular lumen comprises a left atrium.

17. The method of claim 14, wherein the first region comprises a region within the body cavity and at a distance from the lumenal wall of at least 1 cm.

18. The method of claim 1, comprising determining the positions of structural features of the tissue wall comprising relatively raised and/or recessed features; and wherein the produced image also shows said structural features.

19. The method of claim 1, wherein the features shown by the image comprise features of the topography of the tissue wall.

20. The method of claim 1, wherein the tissue wall surrounding the apertures is at a distance from the first region of at least 1 cm.

21. The method of claim 1, wherein the mapping produces a map of the voltage gradients of the electrical field, and the image is generated using the map.

22. The method of claim 1, wherein the one or more electrical field comprises at least three electrical fields crossing within the first region.

23. The method of claim 1, wherein each of the different positions of the probe within the first region is away from a first one of the apertures, said first aperture having a first side facing the first region and second side facing away from the first region, the different positions being on the first side of the first aperture, and the produced image shows a region on the second side of the first aperture.

24. The method of claim 1, wherein the received measurements were obtained using a plurality of electrodes positioned at known distances along the intrabody probe, and the electrical field gradients indicated by the voltage measurements are determined based on the electrical field data and the known distances.

25. The method of claim 1, wherein the voltage gradients comprise a plurality of different local voltage gradients, each at a different one of the different positions.

26. The method of claim 23, wherein the producing the image comprises setting distances from the first region to the first aperture as a function of a decay of a distortion in voltage gradients with distance.

27. The method of claim 1, wherein the different positions of the probe and portions of the image are in respective correspondence, such that each image portion respectively corresponds to a respective position.

28. The method of claim 1, wherein the tissue wall is a wall of a cardiovascular lumen.

29. The method of claim 28, wherein the cardiovascular lumen comprises a left atrium.

30. The method of claim 29, wherein at least one of the apertures is an ostium of a pulmonary vein.

31. The method of claim 29, wherein at least one of the apertures is the mitral valve.

32. The method of claim 1, wherein said measurements comprise voltage measurements made at one or more frequencies within said first region.

\* \* \* \* \*